(12) United States Patent
Larsen et al.

(10) Patent No.: US 7,563,222 B2
(45) Date of Patent: Jul. 21, 2009

(54) METHODS AND APPARATUS FOR INTRAOCULAR BRACHYTHERAPY

(75) Inventors: Charles E. Larsen, Cumming, GA (US); Richard A. Hillstead, Duluth, GA (US); Roelof Trip, Sawanee, GA (US); Eugene deJuan, La Canada Flintridge, CA (US); Mark Humayun, Glendale, CA (US); Eberhard Fritz, Braunschweig (DE); Rainer Pintaske, Pockau (DE)

(73) Assignee: NeoVista, Inc., Fremont, CA (US)

( * ) Notice: Subject to any disclaimer, the term of this patent is extended or adjusted under 35 U.S.C. 154(b) by 553 days.

(21) Appl. No.: 11/228,030

(22) Filed: Sep. 15, 2005

(65) Prior Publication Data
US 2006/0111605 A1  May 25, 2006

Related U.S. Application Data

(63) Continuation-in-part of application No. 11/056,763, filed on Feb. 11, 2005.

(60) Provisional application No. 60/544,001, filed on Feb. 12, 2004.

(51) Int. Cl.
*A61N 5/00* (2006.01)
(52) U.S. Cl. .......................................................... 600/3
(58) Field of Classification Search ................. 600/1–8
See application file for complete search history.

(56) References Cited

U.S. PATENT DOCUMENTS

| 839,061 A | 12/1906 | Farjas |
| 2,517,568 A | 8/1950 | Hissong |
| 2,559,793 A | 7/1951 | Pregel |
| 4,198,570 A | 4/1980 | McHugh et al. |
| 4,584,991 A | 4/1986 | Tokita et al. |
| 4,662,869 A | 5/1987 | Wright .................. 604/22 |
| 4,846,172 A | 7/1989 | Berlin |
| 4,861,520 A | 8/1989 | Van't Hooft et al. |
| 4,891,165 A | 1/1990 | Suthanthiran .................. 600/8 |
| 4,921,327 A | 5/1990 | Zito |
| 4,957,476 A | 9/1990 | Cano |

(Continued)

FOREIGN PATENT DOCUMENTS

DE    199 33 284    1/2001

(Continued)

OTHER PUBLICATIONS

Moore, R. F., "Choroidal Sarcoma Treated by the Intraocular Insertion of Radon Seeds," The British Journal of Ophthalmology (Apr. 1930), vol. 14, pp. 145-152.

(Continued)

*Primary Examiner*—John P Lacyk
(74) *Attorney, Agent, or Firm*—Cook Alex Ltd.

(57) ABSTRACT

A method for performing intraocular brachytherapy and an apparatus for performing the same is disclosed. The apparatus preferably comprises a hand-held delivery device that advances a radiation source into an associated cannula or probe that is positioned adjacent the target tissue. The handpiece provides for shielded storage of the radiation source when retracted from the cannula and includes a slider mechanism for advancing and retracting the radiation source. The radiation source is mounted to a wire that has a flexible distal end and a relatively stiffer proximal end.

7 Claims, 10 Drawing Sheets

U.S. PATENT DOCUMENTS

| | | | |
|---|---|---|---|
| 4,996,159 A | 2/1991 | Glaser | 435/70.3 |
| 5,084,001 A | 1/1992 | Van'tHooft et al. | |
| 5,123,902 A | 6/1992 | Muller et al. | |
| 5,129,895 A | 7/1992 | Vassiliadis et al. | |
| 5,141,487 A | 8/1992 | Liprie | |
| 5,147,282 A | 9/1992 | Kan | |
| 5,183,455 A | 2/1993 | Hayman et al. | |
| 5,199,939 A | 4/1993 | Dake et al. | |
| 5,203,353 A | 4/1993 | Easley et al. | |
| 5,257,988 A | 11/1993 | L'Esperance, Jr. | |
| 5,267,960 A | 12/1993 | Hayman et al. | |
| 5,282,781 A | 2/1994 | Liprie | |
| 5,290,585 A | 3/1994 | Elton | |
| 5,322,499 A | 6/1994 | Liprie | |
| 5,342,283 A | 8/1994 | Good | |
| 5,354,257 A | 10/1994 | Roubin et al. | |
| 5,422,926 A | 6/1995 | Smith et al. | 378/121 |
| 5,425,730 A | 6/1995 | Luloh | 606/15 |
| 5,426,662 A | 6/1995 | Mefferd et al. | 372/99 |
| 5,431,907 A | 7/1995 | Abelson et al. | 424/78.04 |
| 5,487,725 A | 1/1996 | Peyman | |
| 5,503,613 A | 4/1996 | Weinberger | |
| 5,503,614 A | 4/1996 | Liprie | |
| 5,528,651 A | 6/1996 | Leksell et al. | |
| 5,556,389 A | 9/1996 | Liprie | |
| 5,570,408 A | 10/1996 | Gibson | |
| 5,575,749 A | 11/1996 | Liprie | |
| 5,596,011 A | 1/1997 | Repine et al. | 514/369 |
| 5,618,266 A | 4/1997 | Liprie | |
| 5,624,372 A | 4/1997 | Liprie | |
| 5,624,437 A | 4/1997 | Freeman et al. | |
| 5,637,073 A | 6/1997 | Freire | 600/3 |
| 5,651,783 A | 7/1997 | Reynard | 606/4 |
| 5,688,220 A | 11/1997 | Verin et al. | 600/1 |
| 5,707,332 A | 1/1998 | Weinberger | |
| 5,713,828 A | 2/1998 | Coniglione | |
| 5,728,042 A | 3/1998 | Schwager | |
| 5,729,583 A | 3/1998 | Tang et al. | 378/122 |
| 5,738,677 A | 4/1998 | Colvard et al. | |
| 5,772,642 A | 6/1998 | Ciamacco, Jr. et al. | |
| 5,782,740 A | 7/1998 | Schneiderman | |
| 5,797,889 A | 8/1998 | Steinman | |
| 5,807,231 A | 9/1998 | Liprie | |
| 5,830,173 A | 11/1998 | Avery et al. | |
| 5,833,593 A | 11/1998 | Liprie | |
| 5,836,882 A | 11/1998 | Frazin | |
| 5,854,822 A | 12/1998 | Chornenky et al. | |
| 5,855,546 A | 1/1999 | Hastings et al. | |
| 5,857,956 A | 1/1999 | Liprie | |
| 5,863,284 A | 1/1999 | Klein | |
| 5,865,720 A | 2/1999 | Hastings et al. | |
| 5,879,333 A | 3/1999 | Smith | |
| 5,882,291 A | 3/1999 | Bradshaw et al. | |
| 5,885,279 A | 3/1999 | Bretton | |
| 5,899,882 A | 5/1999 | Waksman et al. | |
| 5,904,144 A | 5/1999 | Hammang et al. | 128/898 |
| 5,913,813 A | 6/1999 | Williams et al. | |
| 5,924,974 A | 7/1999 | Loffler | |
| 5,928,130 A | 7/1999 | Schmidt | |
| 5,947,958 A | 9/1999 | Woodard et al. | |
| 5,957,829 A | 9/1999 | Thornton | |
| 5,976,106 A | 11/1999 | Verin et al. | 604/96 |
| 5,984,853 A | 11/1999 | Smith | |
| 6,004,269 A | 12/1999 | Crowley et al. | |
| 6,004,279 A | 12/1999 | Crowley et al. | |
| 6,019,718 A | 2/2000 | Hektner | |
| 6,024,690 A | 2/2000 | Lee et al. | |
| 6,030,333 A | 2/2000 | Sioshansi et al. | 600/3 |
| 6,033,357 A | 3/2000 | Ciezki et al. | |
| 6,036,631 A | 3/2000 | McGrath et al. | |
| 6,041,252 A | 3/2000 | Walker et al. | 604/20 |
| 6,050,930 A | 4/2000 | Teirstein | 600/3 |
| 6,053,858 A | 4/2000 | Bueche et al. | |
| 6,059,713 A | 5/2000 | Urick et al. | |
| 6,059,752 A | 5/2000 | Segal | |
| 6,059,828 A | 5/2000 | Peyman | |
| 6,069,938 A | 5/2000 | Chornenky et al. | |
| 6,071,227 A | 6/2000 | Popowski et al. | 600/3 |
| 6,074,338 A | 6/2000 | Popowski et al. | 600/3 |
| 6,093,142 A | 7/2000 | Ciamacco, Jr. | |
| 6,095,966 A | 8/2000 | Chornenky et al. | |
| 6,099,457 A | 8/2000 | Good | |
| 6,099,499 A | 8/2000 | Ciamacco, Jr. | |
| 6,102,844 A | 8/2000 | Ravins et al. | 600/8 |
| 6,106,454 A | 8/2000 | Berg et al. | |
| 6,108,402 A | 8/2000 | Chornenky | |
| 6,111,932 A | 8/2000 | Dinsmore | 378/136 |
| 6,117,480 A | 9/2000 | Spallek et al. | |
| 6,134,294 A | 10/2000 | Gibbs | 378/65 |
| 6,142,994 A | 11/2000 | Swanson et al. | |
| 6,146,322 A | 11/2000 | Papirov et al. | 600/3 |
| 6,149,574 A | 11/2000 | Trauthen et al. | |
| 6,149,931 A | 11/2000 | Schwartz et al. | 424/427 |
| 6,159,140 A | 12/2000 | Loeffler et al. | |
| 6,162,165 A | 12/2000 | Apple et al. | |
| 6,163,947 A | 12/2000 | Coniglione | |
| 6,164,281 A | 12/2000 | Zhao | 128/898 |
| 6,179,768 B1 | 1/2001 | Loffler et al. | |
| 6,181,770 B1 | 1/2001 | Ciravolo et al. | 378/117 |
| 6,183,410 B1 | 2/2001 | Jacobsen et al. | |
| 6,195,411 B1 | 2/2001 | Dinsmore | |
| 6,196,963 B1 | 3/2001 | Williams | |
| 6,198,804 B1 | 3/2001 | Dinsmore | |
| 6,203,524 B1 | 3/2001 | Burney et al. | |
| 6,210,312 B1 | 4/2001 | Nagy | |
| 6,210,315 B1 | 4/2001 | Andrews et al. | 600/7 |
| 6,213,932 B1 | 4/2001 | Schmidt | |
| 6,224,536 B1 | 5/2001 | Pike | |
| 6,231,494 B1 | 5/2001 | Verin et al. | 600/1 |
| 6,234,951 B1 | 5/2001 | Hastings | |
| 6,241,651 B1 | 6/2001 | Smith et al. | |
| 6,245,047 B1 | 6/2001 | Feda et al. | 604/192 |
| 6,258,019 B1 | 7/2001 | Verin et al. | 600/1 |
| 6,264,599 B1 | 7/2001 | Slater et al. | 600/7 |
| 6,273,850 B1 | 8/2001 | Gambale et al. | |
| 6,283,910 B1 | 9/2001 | Bradshaw et al. | |
| 6,283,911 B1 | 9/2001 | Keren | |
| 6,284,751 B1 | 9/2001 | Aiello et al. | 514/183 |
| 6,285,735 B1 | 9/2001 | Sliski et al. | 378/65 |
| 6,289,079 B1 | 9/2001 | Chornenky et al. | |
| 6,293,899 B1 | 9/2001 | Sioshansi et al. | 600/3 |
| 6,299,054 B1 | 10/2001 | Gibbs, Jr. | 228/164 |
| 6,301,328 B1 | 10/2001 | Sliski et al. | 378/65 |
| 6,302,581 B1 | 10/2001 | Sliski et al. | 378/198 |
| 6,306,074 B1 | 10/2001 | Waksman et al. | |
| 6,312,374 B1 | 11/2001 | von Hoffmann | |
| 6,312,393 B1 | 11/2001 | Abreu | 600/558 |
| 6,320,932 B2 | 11/2001 | Dinsmore | |
| 6,320,935 B1 | 11/2001 | Shinar et al. | 378/119 |
| 6,338,709 B1 | 1/2002 | Geoffrion et al. | |
| 6,347,244 B1 | 2/2002 | Dubnack | 600/476 |
| 6,352,501 B1 | 3/2002 | Urick | |
| 6,354,989 B1 | 3/2002 | Nudeshima | |
| 6,359,963 B1 | 3/2002 | Cash | 378/65 |
| 6,377,846 B1 | 4/2002 | Chornenky et al. | |
| 6,378,526 B1 | 4/2002 | Bowman et al. | |
| 6,387,035 B1 | 5/2002 | Savage et al. | |
| 6,391,026 B1 | 5/2002 | Hung et al. | |
| 6,395,294 B1 | 5/2002 | Peyman | 424/422 |
| 6,397,849 B1 | 6/2002 | Bowman et al. | |
| 6,402,676 B2 | 6/2002 | Peterson | |
| 6,409,651 B1 | 6/2002 | Brown, III | |
| 6,409,943 B1 | 6/2002 | Lavie et al. | 252/644 |
| 6,415,016 B1 | 7/2002 | Chornenky et al. | |

| Patent No. | Date | Inventor | Class |
|---|---|---|---|
| 6,416,457 B1 | 7/2002 | Urick et al. | 600/3 |
| 6,419,621 B1 | 7/2002 | Sioshansi et al. | 60/3 |
| 6,421,416 B1 | 7/2002 | Sliski et al. | 378/65 |
| 6,422,989 B1 | 7/2002 | Hektner | |
| 6,425,895 B1 | 7/2002 | Swanson et al. | |
| 6,433,012 B1 | 8/2002 | Tuse et al. | 514/532 |
| 6,436,026 B1 | 8/2002 | Sioshansi et al. | 600/3 |
| 6,438,206 B1 | 8/2002 | Shinar et al. | 378/123 |
| 6,442,822 B1 | 9/2002 | Liprie | |
| 6,443,881 B1 | 9/2002 | Finger | 600/1 |
| 6,443,976 B1 | 9/2002 | Flower et al. | 607/88 |
| 6,450,937 B1 | 9/2002 | Mercereau et al. | |
| 6,450,938 B1 | 9/2002 | Miller | |
| 6,458,068 B1 | 10/2002 | Knudsen et al. | |
| 6,458,069 B1 | 10/2002 | Tam et al. | |
| 6,465,954 B1 | 10/2002 | Kerslick et al. | |
| 6,471,630 B1 | 10/2002 | Sioshansi et al. | |
| 6,471,636 B1 | 10/2002 | Sano et al. | |
| 6,473,491 B2 | 10/2002 | Chornenky et al. | |
| 6,480,567 B1 | 11/2002 | Feda et al. | 378/65 |
| 6,482,142 B1 | 11/2002 | Winkler et al. | |
| 6,485,406 B1 | 11/2002 | Ziegler et al. | |
| 6,491,619 B1 | 12/2002 | Trauthen et al. | |
| 6,496,561 B1 | 12/2002 | Meyer et al. | |
| 6,497,646 B1 | 12/2002 | Candelaria et al. | |
| 6,497,647 B1 | 12/2002 | Tucker | |
| 6,506,145 B1 | 1/2003 | Bradshaw et al. | |
| 6,508,754 B1 | 1/2003 | Liprie et al. | |
| 6,514,192 B2 | 2/2003 | Tiren | |
| 6,514,193 B2 | 2/2003 | Kaplan | |
| 6,530,875 B1 | 3/2003 | Taylor et al. | |
| 6,546,077 B2 | 4/2003 | Chornenky et al. | |
| 6,551,291 B1 | 4/2003 | deJuan, Jr. et al. | |
| 6,560,312 B2 | 5/2003 | Cash | |
| 6,561,967 B2 | 5/2003 | Schmidt | |
| 6,575,888 B2 | 6/2003 | Zamora et al. | |
| 6,579,256 B2 | 6/2003 | Hughes | 604/60 |
| 6,582,417 B1 | 6/2003 | Ledesma et al. | |
| 6,603,988 B2 | 8/2003 | Dowlatshahi | |
| 6,607,478 B2 | 8/2003 | Williams | |
| 6,623,418 B2 | 9/2003 | Smith | |
| 6,626,817 B2 | 9/2003 | Luth | |
| 6,632,176 B2 | 10/2003 | McIntire et al. | |
| 6,635,008 B2 | 10/2003 | Liprie | |
| 6,638,205 B1 | 10/2003 | Chan et al. | |
| 6,659,933 B2 | 12/2003 | Asano | |
| 6,676,590 B1 | 1/2004 | Urick et al. | |
| 6,676,607 B2 | 1/2004 | de Juan, Jr. et al. | |
| 6,685,618 B2 | 2/2004 | Tam et al. | |
| 6,689,043 B1 | 2/2004 | McIntire et al. | |
| 6,692,481 B2 | 2/2004 | Guerrero | |
| 6,692,759 B1 | 2/2004 | Wong et al. | |
| 6,709,381 B2 | 3/2004 | Munro, III | |
| 6,714,620 B2 | 3/2004 | Caflisch et al. | |
| 6,719,750 B2 | 4/2004 | Varner et al. | |
| 6,749,553 B2 | 6/2004 | Brauckman et al. | |
| 6,755,776 B1 | 6/2004 | Granados | |
| 6,770,019 B1 | 8/2004 | Fritz et al. | |
| 6,771,737 B2 | 8/2004 | Kerslick et al. | |
| 6,786,905 B2 | 9/2004 | Swanson et al. | |
| 6,799,075 B1 | 9/2004 | Chornenky et al. | |
| 6,810,109 B2 | 10/2004 | Chornenky | |
| 6,866,624 B2 | 3/2005 | Chornenky et al. | |
| 6,875,165 B2 | 4/2005 | deJuan, Jr. et al. | |
| 6,914,960 B2 | 7/2005 | Swanson et al. | |
| 6,953,426 B2 | 10/2005 | Barber et al. | |
| 6,984,230 B2 | 1/2006 | Scheller et al. | |
| 7,018,371 B2 | 3/2006 | Forman | |
| 7,041,047 B2 | 5/2006 | Gellman et al. | |
| 7,070,554 B2 | 7/2006 | White et al. | |
| 7,083,566 B2 | 8/2006 | Tornes et al. | |
| 7,179,912 B2 | 2/2007 | Halbrook et al. | |
| 7,182,726 B2 | 2/2007 | Williams et al. | |
| 7,194,063 B2 | 3/2007 | Dilmanian et al. | |
| 7,208,748 B2 | 4/2007 | Sliski et al. | |
| 7,220,225 B2 | 5/2007 | Dejuan, Jr. et al. | |
| 7,223,225 B2 | 5/2007 | DeJuan, Jr. et al. | |
| 7,223,226 B2 | 5/2007 | Biscotti | |
| 7,273,445 B2 | 9/2007 | Pulido et al. | |
| 7,276,019 B2 | 10/2007 | DeJuan, Jr. et al. | |
| 2001/0002427 A1 | 5/2001 | Verin et al. | 600/1 |
| 2001/0009970 A1 | 7/2001 | Chornenky et al. | |
| 2001/0016027 A1 | 8/2001 | Dinsmore | 378/65 |
| 2001/0021382 A1 | 9/2001 | Ferrara et al. | 424/145.1 |
| 2001/0027261 A1 | 10/2001 | Weinhous et al. | |
| 2001/0036955 A1 | 11/2001 | Gerritsen et al. | 514/369 |
| 2001/0050971 A1 | 12/2001 | Feda et al. | 378/65 |
| 2002/0015957 A1 | 2/2002 | Hageman et al. | 435/6 |
| 2002/0021784 A1 | 2/2002 | Chornenky et al. | |
| 2002/0040015 A1 | 4/2002 | Miller et al. | 514/185 |
| 2002/0049247 A1 | 4/2002 | Chen | 514/410 |
| 2002/0054664 A1 | 5/2002 | Tiren | 378/119 |
| 2002/0054665 A1 | 5/2002 | Tiren | 378/139 |
| 2002/0055666 A1 | 5/2002 | Hunter et al. | |
| 2002/0065448 A1 | 5/2002 | Bradshaw et al. | |
| 2002/0072494 A1 | 6/2002 | Cao | 514/12 |
| 2002/0090053 A1 | 7/2002 | Chornenky et al. | |
| 2002/0106055 A1 | 8/2002 | Cash | 378/65 |
| 2002/0110220 A1 | 8/2002 | Shen et al. | 378/124 |
| 2002/0115902 A1 | 8/2002 | Dejuan, Jr. et al. | 600/3 |
| 2002/0146090 A1 | 10/2002 | Chornenky et al. | 378/65 |
| 2002/0156003 A1 | 10/2002 | Lorens et al. | 514/12 |
| 2002/0160954 A1 | 10/2002 | Hageman et al. | 514/12 |
| 2002/0160979 A1 | 10/2002 | Barnerjee et al. | 514/12 |
| 2002/0172829 A1 | 11/2002 | Mori et al. | |
| 2002/0183253 A1 | 12/2002 | Brazzell et al. | 514/12 |
| 2002/0183302 A1 | 12/2002 | Strong et al. | 514/185 |
| 2002/0193326 A1 | 12/2002 | Sukhatme | 514/44 |
| 2003/0144570 A1 | 7/2003 | Hunter et al. | |
| 2003/0158480 A1 | 8/2003 | Tornes et al. | |
| 2003/0179854 A1 | 9/2003 | Jaafar | |
| 2003/0199726 A1 | 10/2003 | Gatto | |
| 2003/0199848 A1 | 10/2003 | Ledesma et al. | |
| 2003/0204125 A1 | 10/2003 | Brauckman et al. | |
| 2003/0208096 A1 | 11/2003 | Tam et al. | |
| 2004/0116767 A1 | 6/2004 | Lebovic et al. | |
| 2004/0199130 A1 | 10/2004 | Chornenky et al. | |
| 2004/0218721 A1 | 11/2004 | Chornenky et al. | |
| 2004/0218724 A1 | 11/2004 | Chornenky et al. | |
| 2004/0225175 A1 | 11/2004 | Moody et al. | |
| 2004/0245483 A1 | 12/2004 | Smit et al. | |
| 2005/0027156 A1 | 2/2005 | Pulido et al. | |
| 2005/0031083 A1 | 2/2005 | Kinklein | |
| 2005/0049508 A1 | 3/2005 | Forman et al. | |
| 2005/0080340 A1 | 4/2005 | Stewart et al. | |
| 2005/0101825 A1 | 5/2005 | Winkler et al. | |
| 2005/0177019 A1 | 8/2005 | DeJuan, Jr. et al. | |
| 2005/0277802 A1 | 12/2005 | Larsen et al. | |
| 2006/0025800 A1 | 2/2006 | Suresh | |
| 2006/0078087 A1 | 4/2006 | Forman et al. | |
| 2006/0084952 A1 | 4/2006 | Pallikaris et al. | |
| 2006/0100475 A1 | 5/2006 | White et al. | |
| 2006/0111605 A1 | 5/2006 | Larson et al. | |
| 2006/0142629 A1 | 6/2006 | Dejuan, Jr. et al. | |
| 2006/0173479 A1 | 8/2006 | Smith | |
| 2006/0189838 A1 | 8/2006 | Dejuan, Jr. et al. | |
| 2006/0204535 A1 | 9/2006 | Johnson | |
| 2006/0217587 A1 | 9/2006 | DiCarlo et al. | |
| 2007/0010746 A1 | 1/2007 | Forman et al. | |
| 2007/0016126 A1 | 1/2007 | Forman et al. | |
| 2007/0055089 A1 | 3/2007 | Larson et al. | |
| 2007/0083129 A1 | 4/2007 | Mark | |
| 2007/0106108 A1 | 5/2007 | Hermann et al. | |
| 2007/0118010 A1 | 5/2007 | Hillstead et al. | |
| 2007/0123815 A1 | 5/2007 | Mark | |
| 2007/0142694 A1 | 6/2007 | Cutrer et al. | |

| | | | |
|---|---|---|---|
| 2007/0142695 A1 | 6/2007 | White et al. | |
| 2007/0166284 A1 | 7/2007 | Rasmussen et al. | |
| 2007/0167664 A1 | 7/2007 | Hermann et al. | |
| 2007/0167665 A1 | 7/2007 | Hermann et al. | |
| 2007/0265485 A1 | 11/2007 | DeJuan, Jr. et al. | |

FOREIGN PATENT DOCUMENTS

| | | |
|---|---|---|
| DE | 10 2005 056 080 A1 | 5/2007 |
| EP | 0 541 699 B1 | 5/1996 |
| EP | 0 778 788 B1 | 5/2003 |
| EP | 1 060 765 B1 | 12/2004 |
| EP | 1 317 945 B1 | 10/2005 |
| EP | 1 369 143 B1 | 12/2005 |
| EP | 1 060 764 B1 | 3/2006 |
| EP | 0 993 843 B1 | 4/2006 |
| EP | 1 529 554 B1 | 8/2006 |
| GB | 1 211 316 | 11/1970 |
| JP | 8131453 | 5/1996 |
| JP | 2000350742 | 12/2000 |
| WO | WO 98/01179 | 1/1998 |
| WO | WO 99/42162 | 8/1999 |
| WO | WO 00/33916 | 6/2000 |
| WO | WO 01/43826 | 6/2001 |
| WO | WO 2005/050393 A2 | 6/2005 |
| WO | WO 2005/079294 A2 | 9/2005 |
| WO | WO 2006/137831 A2 | 12/2006 |
| WO | WO 2007/060051 A1 | 5/2007 |

OTHER PUBLICATIONS

Finger, et al., "Palladium 103 Ophthalmic Plaque Radiotherapy," Arch Ophthalmol. (Nov. 1991), vol. 109, pp. 1610-1613.

Finger, et al., "Palladium-103 versus Iodine-125 for Ophthalmic Plaque Radiotherapy" (1993), Int. J. Radiation Oncology Biol. Phys., vol. 27, pp. 849-854.

Finger, et al., "Ophthalmic Plaque Radiotherapy for Age-Related Macular Degeneration Associated with Subretinal Neovascularization," American Journal of Ophthalmology (1999), vol. 127, No. 2, pp. 170-177.

Sharma, R. K., et al., "Development in Retinal Cell Transplants," Dig J Ophthalmol, Massachusetts Eye and Ear Infirmary (2001), vol. 7(2), Website www.medscape.com/viewarticle/408963.

University of Illinois at Chicago, Office of Technology Management, "Intraocular Brachytherapy Device" (2003), 2 Website Pages—www.vpted.uilllinis.edu/events/iemerging/coas/brachytherapy.

International Search Report for PCT/US 06/31004 dated Jan. 17, 2008.

Flaxel, C.J. et al., "Radiation Treatment in Age-Related Macular Degeneration". Age-Related Macular Degeneration. Ed. Jennifer I. Lim. New York: Marcel Dekker, 2002. 225-238.

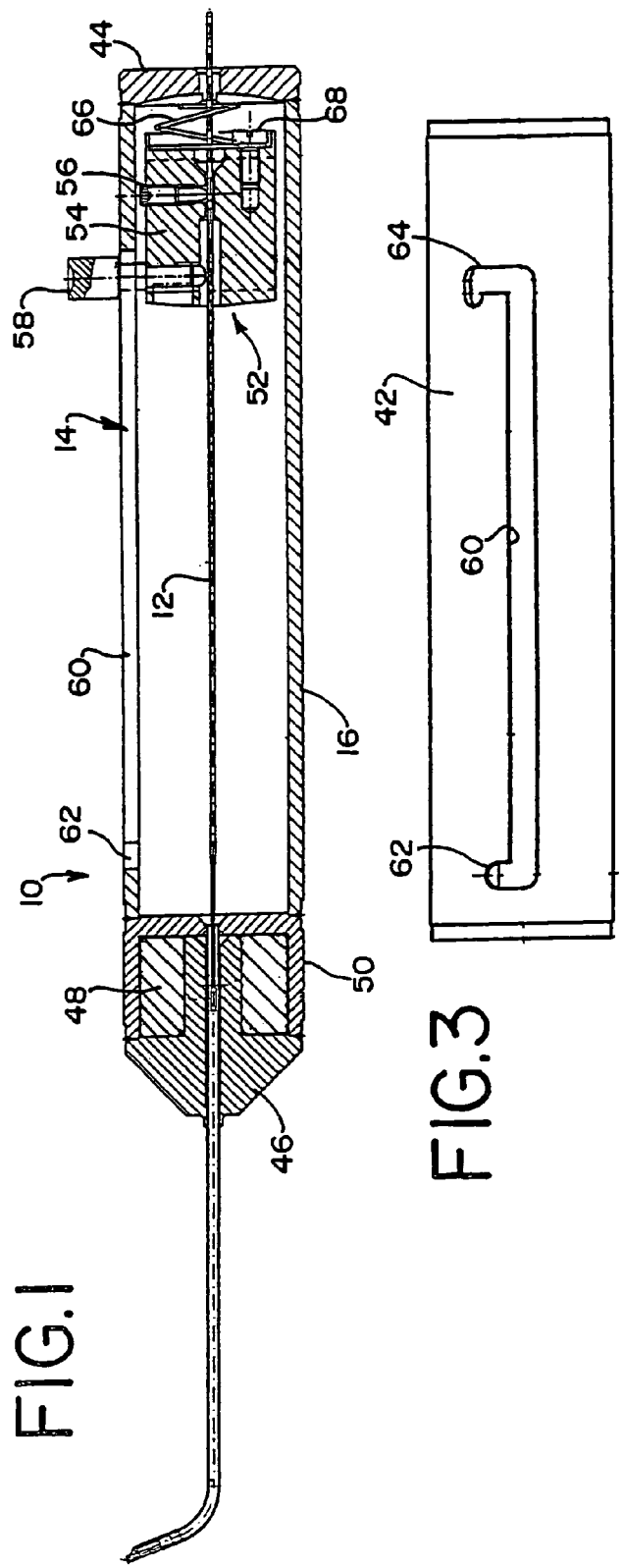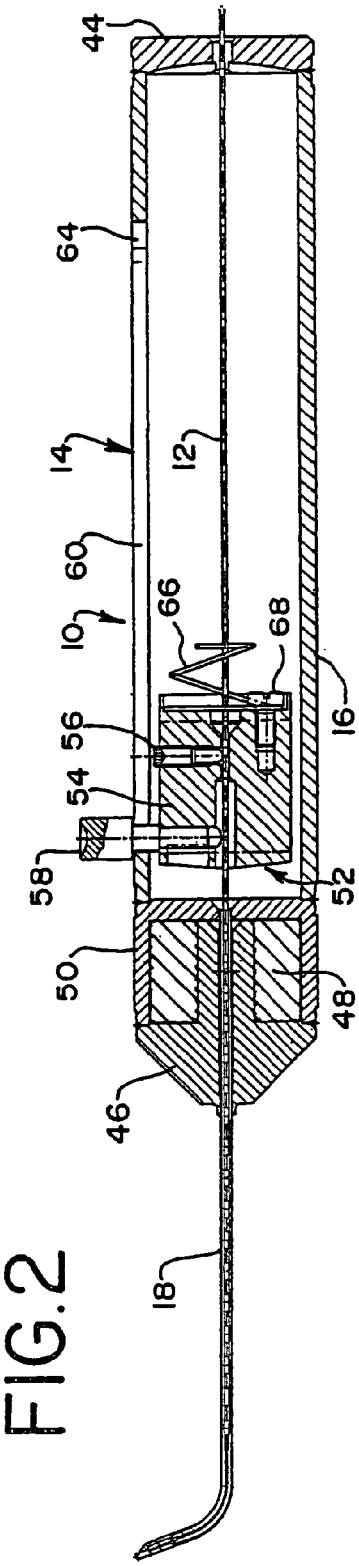

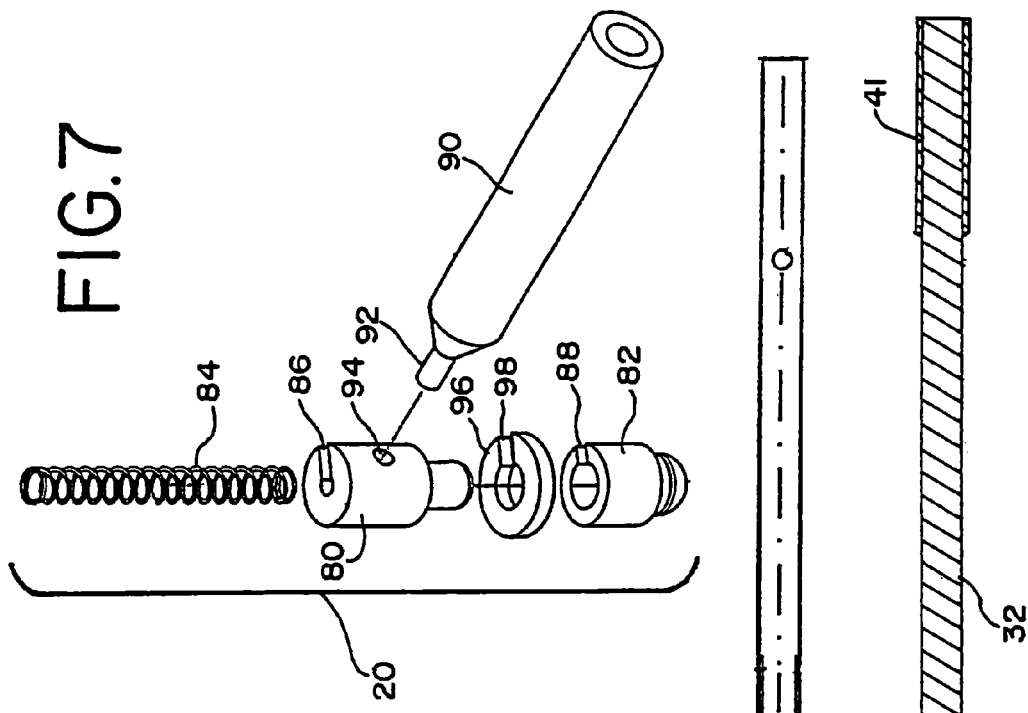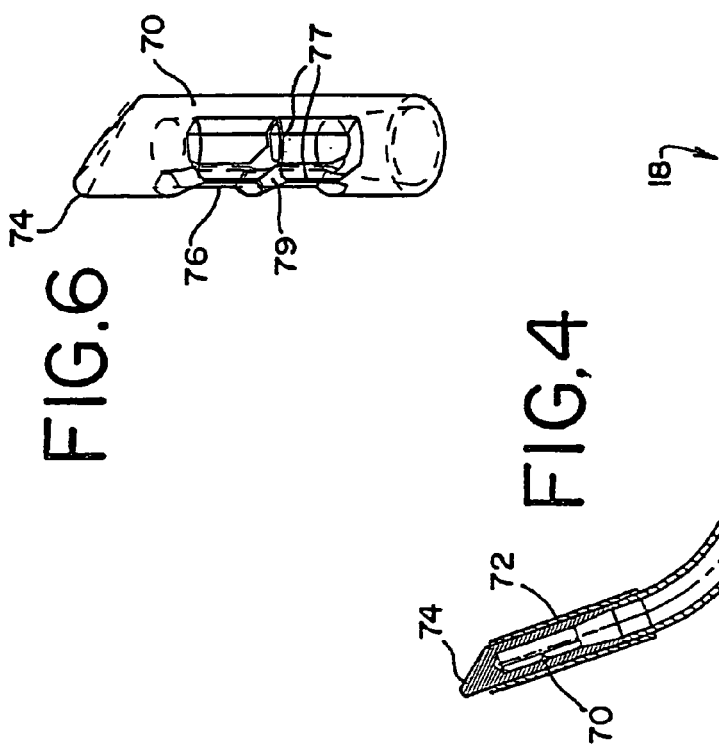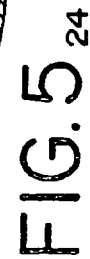

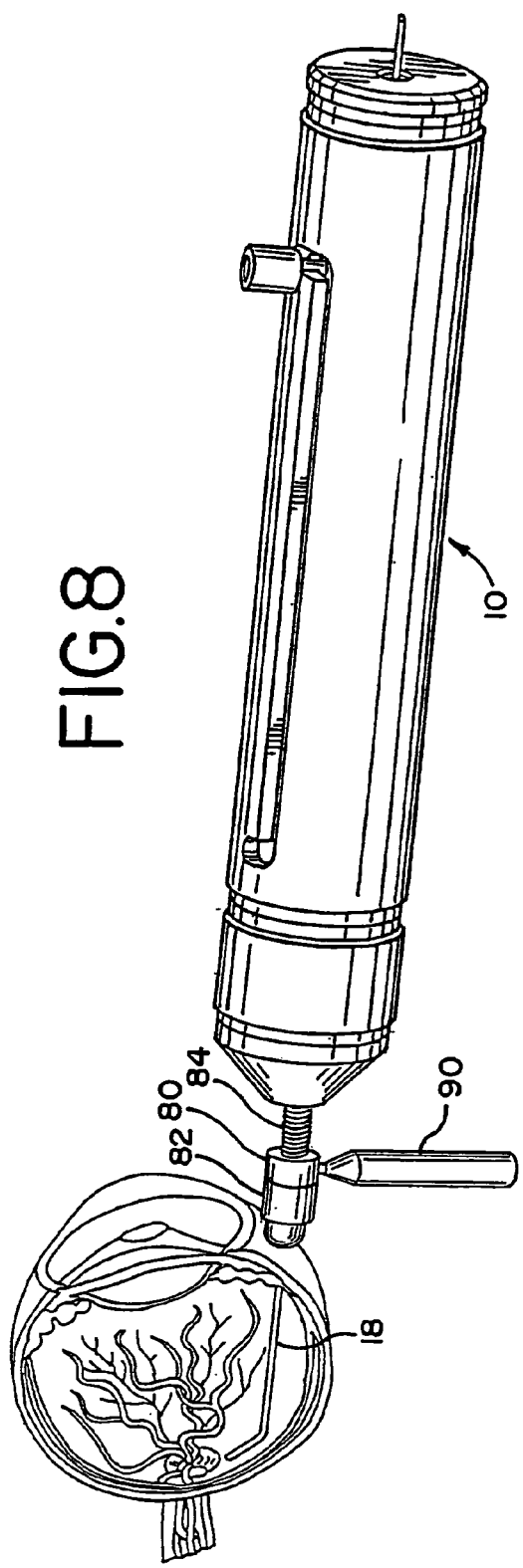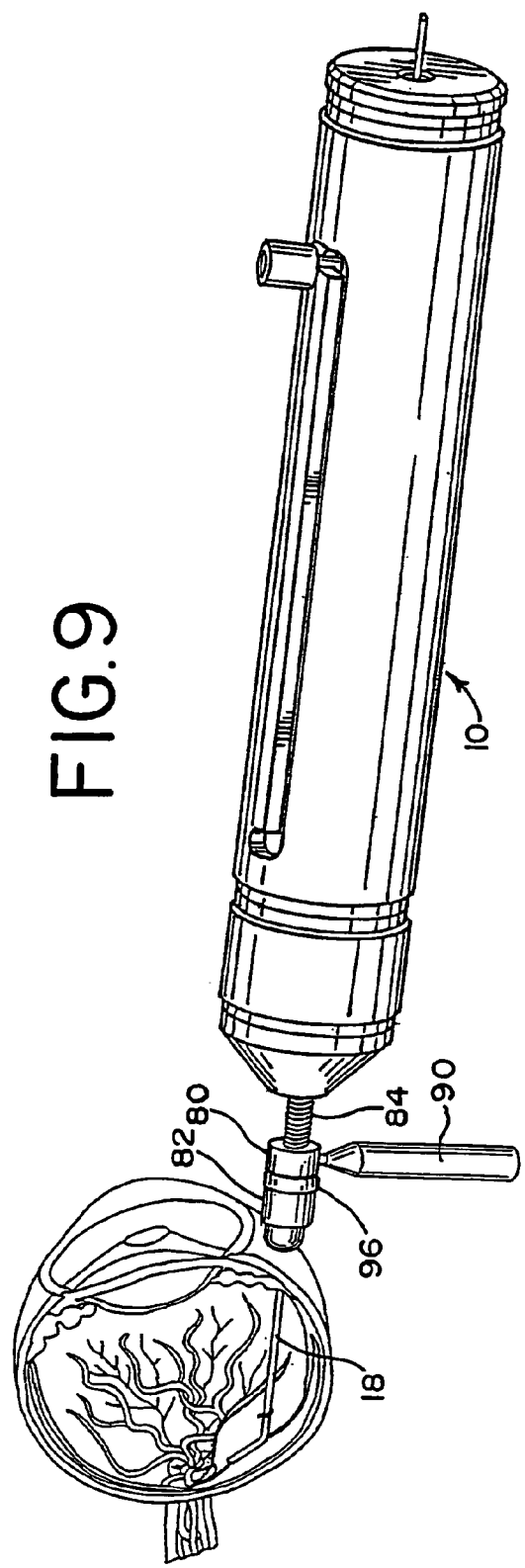

METHODS AND APPARATUS FOR INTRAOCULAR BRACHYTHERAPY

CROSS-REFERENCE TO RELATED APPLICATION

This application is a continuation-in-part of U.S. application Ser. No. 11/056,763, filed Feb. 11, 2005, which, in turn, claims the benefit of the filing date of U.S. Provisional Application Ser. No. 60/544,001, filed Feb. 12, 2004, which are herein incorporated by reference.

BACKGROUND OF THE INVENTION

The present invention relates to apparatus, systems and methods for performing intraocular (i.e., within the eye) brachytherapy. The invention may be employed in the treatment of a variety of eye disorders, but is particularly suited for treatment of macular degeneration in which neovascularized ocular tissue is treated by means a of local, directional delivery of a radiation dose emitted by a radioactive source to target tissues.

The slow, progressive loss of central vision is known as macular degeneration. Macular degeneration affects the macula, a small portion of the retina. The retina is a fine layer of light-sensing nerve cells that covers the inside back portion of the eye. The macula is the central, posterior part of the retina and contains the largest concentration of photoreceptors. The macula is typically 5 to 6 mm in diameter, and its central portion is known as the fovea. While all parts of the retina contribute to sight, the macula provides the sharp, central vision that is required to see objects clearly and for daily activities including reading and driving.

Macular degeneration is generally caused by age (termed Age Related Macular Degeneration or "AMD") or poor circulation in the eyes. Smokers and individuals with circulatory problems have an increased risk for developing the condition. AMD is the leading cause of blindness in people older than 50 years in developed countries. Between the ages of 52-64, approximately 2% of the population are affected. This rises to about 28% of the population over the age of 75.

There are two forms of macular degeneration, which are known as "wet" and "dry" macular degeneration. Dry macular degeneration blurs the central vision slowly over time. Individuals with this form of macular degeneration may experience a dimming or distortion of vision that is particularly noticeable when trying to read. In dry macular degeneration, yellowish deposits called drusen develop beneath the macula. Drusen are accumulations of fatty deposits, and most individuals older than 50 years have at least one small druse. These fatty deposits are usually carried away by blood vessels that transport nutrients to the retina. However, this process is diminished in macular degeneration and the deposits build up. Dry macular degeneration may also result when the layer of light-sensitive cells in the macula become thinner as cells break down over time. Generally, a person with the dry form of macular degeneration in one eye eventually develops visual problems in both eyes. However, dry macular degeneration rarely causes total loss of reading vision.

Wet macular degeneration (which is the neovascular form of the disease) is more severe than dry macular degeneration. The loss of vision due to wet macular degeneration also comes much more quickly than dry macular degeneration. In this form of the disease, unwanted new blood vessels grow beneath the macula (Choroidal Neo-Vascularization (CNV) endothelial cells). These choroidal blood vessels are fragile and leak fluid and blood, which causes separation of tissues and damages light sensitive cells in the retina. Individuals with this form of macular degeneration typically experience noticeable distortion of vision such as, for example, seeing straight lines as wavy, and seeing blank spots in their field of vision.

Early diagnosis of the wet form of macular degeneration is vital. If the leakage and bleeding from the choroidal blood vessels is allowed to continue, much of the nerve tissue in the macula may be killed or damaged. Such damage cannot be repaired because the nerve cells of the macula do not grow back once they have been destroyed. While wet AMD comprises only about 20% of the total AMD cases, it is responsible for approximately 90% of vision loss attributable to AMD.

It has been proposed to provide a device that is particularly suitable for the localized delivery of radiation for the treatment of macular degeneration. See, U.S. Pat. No. 6,875,165 to deJuan, et al., which is incorporated herein by reference. A localized retinal detachment (called a "bleb") is created by performing a retinotomy and injecting saline therethrough using a subretinal infusion needle, thus creating a space between the partially-detached retina and the area of chloridal neo-vascularization. A radiation-emitting source is introduced into the bleb and the CNV is directly irradiated. The exposure of the new blood vessels formed during the wet form of macular degeneration to radiation provides sufficient disruption of the cellular structures of the new blood cell lesions to reverse, prevent, or minimize the progression of the macular degeneration disease process. Such therapy can potentially restore visual acuity, extend retention of visual acuity or slow the progressive loss of visual acuity.

The present application relates to advances in apparatus, systems and methods for performing intraocular brachytherapy, in general, and for the treatment of macular degeneration with a subretinal or an epiretinal application of radiation, in particular.

BRIEF DESCRIPTION OF THE DRAWINGS

FIG. 1 is a partial longitudinal cross-sectional view of an apparatus for performing intraocular brachytherapy comprising a handpiece, a cannula secured to the handpiece, and a radiation source wire ("RSW") interior of the handpiece and cannula in a retracted position.

FIG. 2 is a cross-sectional view of the apparatus of FIG. 1 with the radiation-emitting element advanced to the treatment position.

FIG. 3 is a top view (as compared to FIGS. 1 and 2) of a portion of the housing comprising part of handpiece shown in FIG. 1.

FIG. 4 is an enlarged view of the cannula associated with the system of FIG. 1, in partial cross-section.

FIG. 5 is a fragmentary, cross-sectional view of the radioactive source wire forming a portion of the system shown in FIG. 1.

FIG. 6 is a perspective view of the distal end of the cannula and a dose flattening filter comprising a portion of the tip or distal end of the cannula.

FIG. 7 is an exploded perspective view of a first embodiment of a positioning system for use with the system of FIG. 1.

FIGS. 8 and 9 illustrate the use of the positioning system of FIG. 7 in connection with the system of FIG. 1.

DETAILED DESCRIPTION

Figure 10:
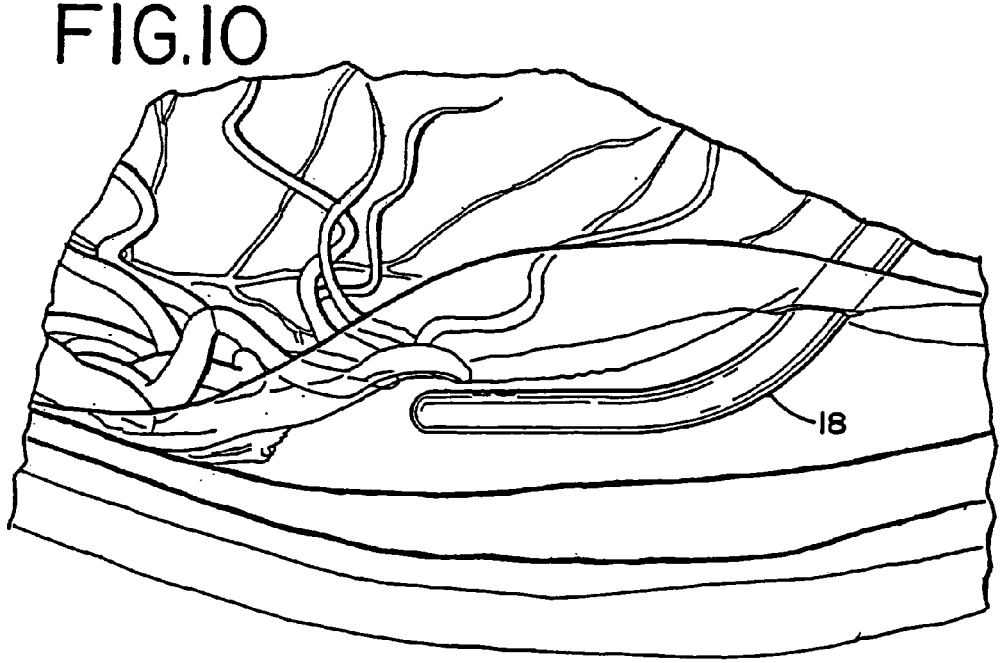
FIG. 10 is an enlarged view showing the treatment of CNV with the device of FIG. 1.

In the intraocular treatment of AMD, vitreoretinal surgical techniques are used to facilitate placement of a radioactive source that preferably, but not exclusively, emits beta or other ionizing radiation, such as gamma or X-ray radiation, temporarily in a subretinal space (with detachment of the retina to gain access to the subretinal space) or an epiretinal space (which does not require detachment of the retina and where the radiation may be transmitted through the retina to the underlying target area) by means of an intraocular cannula, sheath or probe. Other non-ionizing radiation sources, such as light or heat sources, as circumstances require, may also be used.

In accordance with one aspect of the present invention, an apparatus is provided employing the radioactive source and a delivery device that permits movement of the source between a stored position and treating position. When in the stored (retracted) position, the radiation source is surrounded by a suitable material, such as a stainless steel and lead lining, that effectively protects the surgeon and patient during handling and initial positioning. If radiation is being applied subretinally, the source is preferably located within a specially designed tip of platinum iridium (Pt/Ir), or other suitable material, that provides for directional administration of the radiation with controlled intensity, while shielding and protecting the retina and other surrounding non-target tissues.

With reference to FIGS. 1 and 2, the system, generally designated 10, includes two main components: a radiation source, which may be located at the distal end of a source wire (RSW) 12 and a delivery device 14 that comprises, in the illustrated embodiment, a handle 16 and a delivery cannula 18 (also called a sheath or probe). In addition, a positioning system 20, shown in FIG. 7, and method, illustrated in FIGS. 8 and 9, are provided to assist in the precise positioning of the device within the eye.

Radiation source is broadly defined herein, and is not limited to ionizing radiation, light radiation, or heat radiation. For example, the radiation source is intended to include a treatment source of any of a variety of treatment regimens, including ionizing radiation. The radiation source for the RSW 12 comprises any suitable radiation source, including radioactive materials such as gamma and beta emitters, x-ray (e.g., miniaturized x-ray generators), and non-ionizing radiation sources, such as laser or other light sources. Alternatively, ultrasound, heat, cryo-ablation, or microwave sources may also be utilized.

Preferably, an ionizing radiation source of an essentially beta emitting material, such as a Strontium/Yttrium 90 (Sr-90/Y-90) beta emitting isotope, is used. With a source activity of approximately 11 mCi and a subretinal location for the radiation source of about 1-3 mm from the target tissue (preferably about 1-1.5 mm), the treatment duration is relatively short, approximately 2-4 minutes. The system and method provide for the delivery of radiation at the site of the choroidal neovascularization that occurs in macular degeneration, or other treatment site. When employing subretinal ionizing radiation, the system preferably provides radiation to a target site at a dose rate of from approximately 4 to 20 GY/min; with a preferred target dose of between approximately 10 and 40 GY, with the target dose more preferably being approximately 26 GY for neovascularized tissue.

As illustrated in FIG. 5, the preferred embodiment of the radiation source includes a cylindrical aluminum insert 22 that is doped with the Sr-90/Y-90 isotope in accordance with conventional techniques and preferably resides inside a sealed stainless steel canister. The canister comprises a seed tubing 24 sealed on its distal end with a lid 26 and on its proximal end with a lid 28. The stainless steel canister may be mounted to a solid or braided wire made of stainless steel (or other material) to form the RSW 12 that is used to advance the source to and retract the source from the treatment location.

As shown in FIG. 5, the radioactive source wire 12 preferably includes a relatively flexible distal or leading strand 30 and a relatively stiffer proximal or handle strand 32. Specifically, the flexibility of the leading strand 30 is such as to allow unimpeded mechanical transport through the cannula 18 around a radius of curvature of from 4 to 8 mm. The RSW 12 has an overall length on the order of 190 mm, which provides a 10 mm-15 mm protrusion of the wire from the rear of the handle 16 (as seen in FIGS. 1 and 2) when the RSW 12 is advanced to the treatment position, thus providing for removal or repositioning of the RSW, if necessary.

The distal end of the leading strand 30 includes a connection tubing 34 closed by a lid 36 for facilitating attachment of the canister housing the radioactive insert 22. A further connection tubing 38 is used to join the proximal end of the leading strand 30 to the distal end of the handle strand 32. In the illustrated embodiment, the leading strand 30 has a smaller outside diameter than the handle strand. Thus, the proximal end of the leading strand 30 carries an additional length of tubing 40 to build up the outside diameter of the leading strand 30 to match that of the handle strand. The proximal end of the handle strand 32 also includes a length of tubing 41 for reinforcement. Other than the radioactive insert 22, the various components of the RSW 12 are preferably made of stainless steel and are joined together by laser welding. Other means for delivering and/or retrieving the radioactive source, as disclosed in the prior art, may also be used. For example, the radioactive source may not be secured to a wire, and movement of the source canister between treatment and storage positions can be accomplished pneumatically or hydraulically. See, e.g., U.S. Pat. No. 5,683,345, which is incorporated herein by reference.

The delivery device 14 is preferably, but not necessarily, handheld to facilitate control and positioning of the delivery cannula 18 during use. When not in use, the radiation source 22, e.g., a beta radiation source, may be positioned inside the shielded storage handle 16. The handle 16 includes a slider mechanism to which a proximal portion of the RSW 12 is secured, the slide mechanism being moveable between treatment position (FIG. 2), in which the radioactive source 22 is positioned at the distal end of the cannula 18, and a retracted position (FIG. 1) for storage of the radioactive source 22 within the handle 16. While in the storage position, the radiation source is preferably shielded by a combination of stainless steel (inner shield) and lead (outer shield). The stainless steel shield blocks the beta radiation, while the lead shield reduces the secondary radiation (known as brehmsstrahlung). Other suitable materials may also be used for shielding.

With reference to FIGS. 1-3, the handle 16 comprises a multi-part housing with an elongated cylindrical case 42 closed at its proximal end by end cap 44 and at its distal end by a central hub 46, to which the cannula 18 is secured. The hub 46 is preferably made of stainless steel and serves as the inner radiation shield for the radioactive source when in the storage position. The wall thickness of the shielding portion of the hub is approximately 1.9 mm. The hub 46 also carries the lead outer shield, designated 48, which has a wall thickness of approximately 4.6 mm. The hub 46 and outer shield 48 are carried by a cup-like retaining member 50 that is secured to the distal end of the case 42.

As noted above, the handle 16 includes an advancement or positioning mechanism (also referred to as a slider mechanism), generally designated 52, for moving the radioactive source 22 between the storage and treatment positions. The slider mechanism 52 includes a carrier member 54 that is slidingly received on the interior of the cylindrical case 42 of the handle 16. The carrier 54 includes a central aperture, through which the handle strand 32 of the RSW 12 extends, with the RSW 12 being secured to the carrier 54 by means of a set screw 56.

For moving the carrier 54 between the proximal and distal ends of the case 42, an actuator pin 58 that extends through an elongated slot 60 in the case 42 is secured to the carrier 54. As illustrated, the slot 60 lies in a plane defined by the curved cannula 18, thus having the same orientation as the cannula curve. The slot 60 permits approximately 60 mm, or less, of travel for the carrier 54 and includes offsets 62, 64 at its distal and proximal ends, respectively, for receiving the actuator pin 58, thus providing positive visual and tactile indications of the radioactive source 22 being located in the treatment and storage positions. The proximal side of the carrier 54 also includes a coil spring 66 secured thereto by screw 68 for biasing the actuator pin into a locked condition within proximal offset 64 when in the retracted position.

With reference to FIG. 4, the intraocular probe 18 is preferably an integral part of the delivery device, and is fabricated of a rigid material, such as stainless steel. The probe, or cannula, in the illustrated embodiment, comprises a single lumen and is sealed at the distal end to prevent contact between the radiation source and the patient or the patient's bodily fluids. More particularly, the distal end of the probe includes an inner sleeve 70 (best seen in FIG. 6) in which the radiation source is located when in the treatment position. The inner sleeve 70 is configured to provide a desired dose profile, which is discussed in greater detail below. The inner sleeve 70 is received in a cover sleeve 72 that serves to seal the inner sleeve 70 and also provides some radiation attenuation.

The distal end of the cannula 18 is curved or bent at an angle to facilitate proper alignment of the radiation source and the treatment area. The tip 74 of the probe 18 also preferably has a rounded wedge shape to facilitate positioning of the distal end under the retina, when the retina is partially detached and raised to form a "bleb" (as by injection of saline or other liquid under the retina) during the performance of the method.

Figure 11:
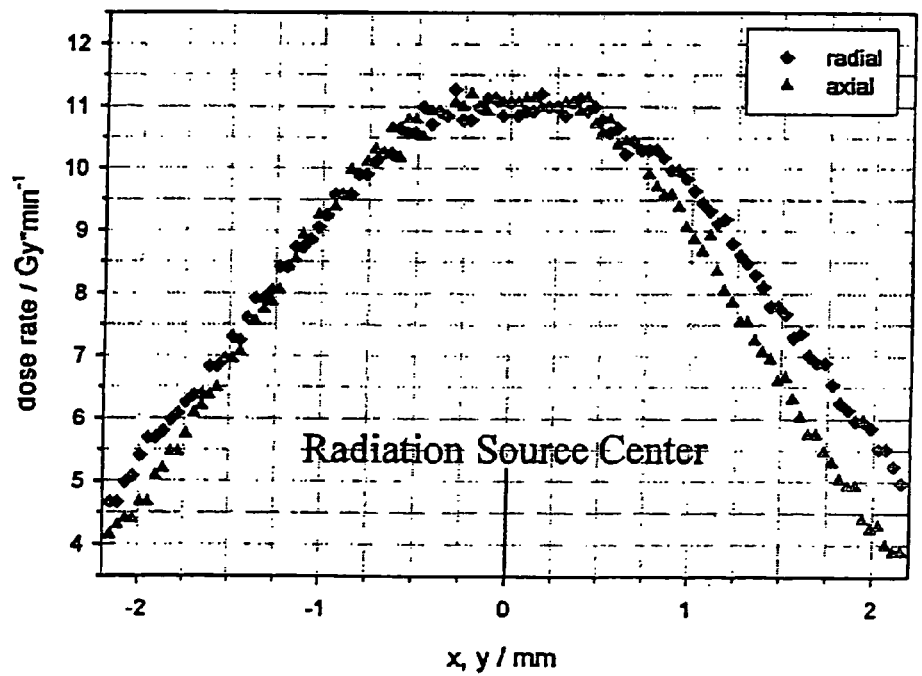
FIG. 11 shows the dose rate profile at the treatment side of the delivery device.

The treatment side of the tip includes a molded, machined or otherwise formed window 76 (sealed by the cover sleeve 72) that allows for directional administration of radiation. The window 76 is subdivided into four smaller windows by longitudinal and transverse splines 77 that intersect at centrally located solid area 79 that acts as a flattening filter to reduce the peak radiation from the source 22 received by tissue closest to the radiation source. As a result, the tissue to be irradiated at the treatment site receives a more uniform dosage. This flattening effect is shown in FIG. 11, which plots the dose rate (in GY/min) as a function of radial and axial distance from the radiation source center. As can be seen in FIG. 11, the peak dose rate is generally flat at the center of the source, and decreases essentially linearly as the distance from the center increases. Various structures of the flattening filter are discussed in the co-pending PCT application "Radioactive Radiation Source for Ophthalmic Brachytherapy," PCT/EP2004/012415, filed Nov. 3, 2004, WO 2005/049139 A1, which is incorporated herein by reference. In general, the flattening filter preferably comprises a shield of selected thickness and/or material suspended in the window at the point closest the treatment site that attenuates or blocks a portion of the radiation from escaping the probe.

A first embodiment of a system 20 for precise positioning of the probe 18 is shown in FIG. 7. The positioning system 20 is adapted to space the probe tip a set distance away from the target tissue and, as such, is particularly suited for the subretinal approach. The positioning system 20 comprises a base 80 and contact extension 82 which serve as a reference member and are adapted to be mounted to the extra-ocular portion of the sheath or probe 18. Using the sclera (the surface of the eye) as a dimensional reference point or surface, a spring 84 is located on the probe 18 to provide a positive engagement of the contact extension 80 (when carried on the base 82) against the sclera during initial placement. See FIGS. 8 and 9.

For purposes of assembly onto the probe, the base 80 has a slot 86 sized to fit over the probe 18 so that it can be placed thereon. The contact extension 82 also has a slot 88 thereon to facilitate placement on the probe 18 distally of the base 80. The contact extension 82 designed to seat on the base 80 and is maintained in position thereon by frictional engagement. A handle 90 is provided that has a threaded end 92 that is received in a complimentarily-threaded aperture 94 in the base 80. The threaded end 92 of the handle 90 serves as a set screw to secure the base 80 in position on the probe 18 after initial placement, as will be discussed in greater detail below. The positioning system 78 may be made of any suitable material, but is preferably made of acetal.

With reference to FIG. 8, the probe is initially positioned, with the tip 74 of the probe in light contact with the target area to be irradiated, touching either the retina or the retinal pigment epithelium (RPE) tissue under the retina. The spring 84 pushes the contact extension 82 mounted on the base 80 into contact with the sclera. The handle 90 is then turned to engage against the probe 18, thus locking the base 80 into position on the probe 18. The probe 18 is then withdrawn from the eye. With the base 80 locked in position on the probe, a spacer 96, which also has a slot 98 that permits it to be placed on the probe 18, is then placed between the base 80 and the contact extension 82, as seen in FIG. 9, to accurately set the distance between the treatment area and the probe tip 74.

In practice, the spacer 96 has a thickness of from about 0.5 to 3 mm, and preferably 1-1.5 mm (more preferably 1 mm), so as to create a space of the same distance between the tip 74 of the probe 18 and the target area. The particular spacing may vary with the eye disorder treated, the radiation source being used, and the size of the treatment area. A spacing of 1-2 mm (and preferably 1.5 mm) is the anticipated spacing for treating the neovascularized tissue associated with macular degeneration with a beta radiation source as described earlier. During the radiation delivery, the contact extension rests against the sclera, resisting or preventing further axial movement of the delivery device into the eye.

Alternatively, positioning of the probe tip can be facilitated by the use of intra-ocular ultrasound or doppler measurement of the distances between the distal end of the cannula and the target tissue. In such cases, the distal end of the cannula may include an ultrasound or doppler transducer (communicating with a read-out device) to both transmit and receive ultrasound or doppler waves. The data generated thereby is analyzed in real time, and a calculated measurement of the distance is presented on an optical readout or indicator. In a similar manner, optical interferometry devices and techniques can be employed for measuring the distance between the cannula tip and the target tissue.

Figure 12:
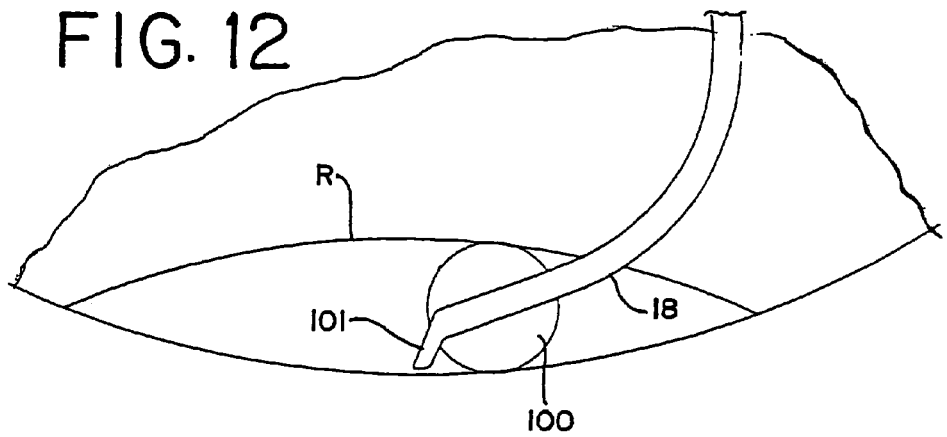
FIG. 12 is a schematic view of a further version of the cannula for use in the present invention having an inflatable balloon at its distal end.

Structures for assuring the proper spacing of the probe tip from the target site can take other forms. For example, as shown in FIG. 12, the tip of the probe 18 may include one or more balloons 100 that are inflatable upon locating the probe tip under the retina (R) in the bleb to insure for spacing of the probe tip between the retina and treatment zone. In addition, or alternatively, the distal end 101 of the probe 18 can be at an angle with respect to the axis of the probe where the radioactive source is located when in the treatment position (again shown in FIG. 12—see also FIGS. 15 and 17). The angled distal end 101 insures that a pre-determined minimum distance is maintained between the radioactive source and the target tissue.

Figure 13:
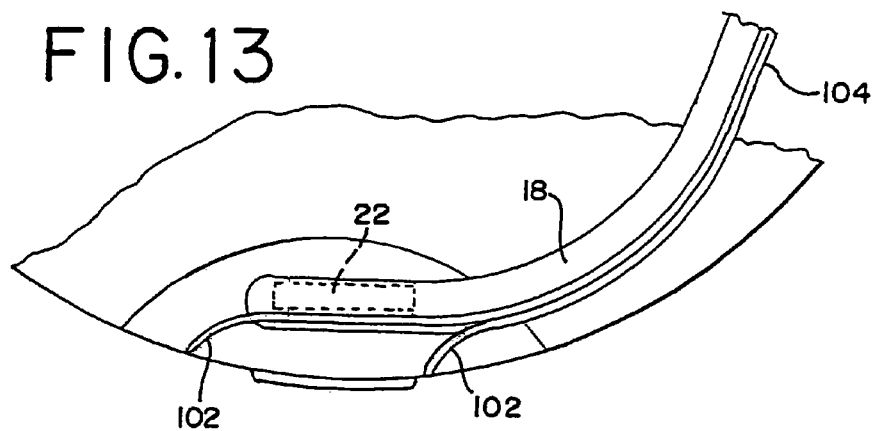
FIG. 13 is a schematic view of an alternate embodiment of the cannula of FIG. 1 including retractable wires for properly spacing the treatment end of the cannula and the radioactive source from the target tissue.
Figure 14:
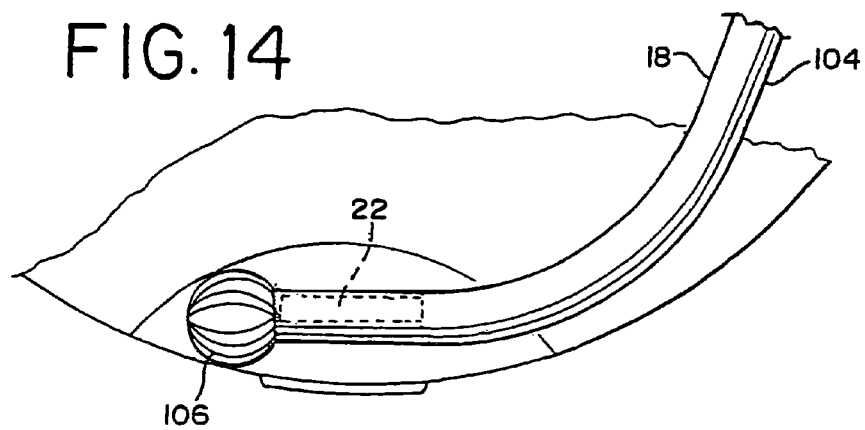
FIG. 14 is a schematic view of an alternate version of the cannula in which a retractable wire basket is provided for maintaining the proper spacing of the radiation source with respect to the target tissue.

In a second alternative, shown in FIG. 13, a preformed wire, or series of wires 102, are extendable from a lumen 104 in the probe to properly space or bump-off the probe tip from the treatment zone when advanced out of the lumen. A further alternative, shown in FIG. 14, is to use a retractable wire basket 106 that is advanced through a lumen 104 in the probe when the probe is placed at the treatment site. A still further alternative is to secure a optic fiber to the probe that extends beyond the distal end an amount corresponding to the desired spacing. When the optic fiber contacts the target tissue, the fiber darkens, thus alerting the surgeon to the desired spacing. The basic procedure for sub-retinal intraocular brachytherapy according to the present invention is accomplished through standard vitrectomy and retinal detachment techniques, with the basic steps as follows. Prior to treatment, the surgeon confirms the location of the target tissue using retinal vascular landmarks and identifies the preferred location of the sclerotomy entry point (i.e., temporal, nasal, etc.) in order to limit exposure of the fovea during treatment. The surgeon will also want to confirm that the radiation source is properly positioned in the probe, when advanced to the treatment position. A device for testing for the proper positioning of the radiation source, and the method of its use, is disclosed in the co-pending PCT application, "Test Device for Testing Positioning of a Radioactive Source and Method of Using Same," PCT/EP2004/012416, filed Nov. 3, 2004, WO 2005/049140 A1, which is herein incorporated by reference.

Then the subject is prepared pursuant to standard vitrectomy procedures. Specifically, the pupil of the subject is dilated and the patient is positioned ventrally on the operating table. After appropriate cardiac and respiratory monitoring is established, and appropriate anesthesia is induced, the eye is anesthetized, such as with a retrobulbar or peribulbar anesthesia.

Next, the treatment area is accessed. A speculum is placed to secure the eye lid, and surgery typically begins with a conjunctival incision into the superotemporal, superonasal and inferotemporal quadrants of the eye to be treated. A scleral incision is made approximately 3 to 4 mm away from the surgical limbus in the inferotemporal quadrant, and an infusion cannula is inserted into the vitreous cavity. After confirming that the infusion cannula is positioned properly, the infusion line is opened and a second and third scleratomy are created 3 to 4 mm away from the surgical limbus in locations determined prior to commencement of the surgery in the superonasal quadrant. An appropriate lens for vitreoretinal surgery is positioned and a vitrectomy performed, a standard endoilluminator (a fiber optic light source) being used to illuminate the vitreous cavity.

Next, the treatment probe is positioned. As can be appreciated, any of a number of different positioning techniques as described herein may be used. If the positioning system as illustrated in FIGS. 7-9 is used, the spring 84 of the positioning system 20 is carefully slid over the probe 18 up to the device handle 16, and the positioning system is placed on to the probe shaft without the spacer element 96. See FIG. 8. The sclerotomy is extended to a length of approximately 1.0-1.3 mm, and the delivery probe is inserted through the sclerotomy incision into the vitreous cavity.

Under microscopic visualization, the surgeon places the tip of the probe directly above the macula. Specifically, the probe is positioned by gently touching the retinal tissue, while directly holding the probe center marker (a mark on the probe tip designating the center of the radiation source) above the center of the CNV complex. While the surgeon holds the probe steady at this position, the positioning system (base 80 and contact extension 82) without the spacer 96 is secured onto the external portion of the delivery probe while in contact with the sclera to identify the precise location of the probe as it contacts the retina by tightening the handle, and the cannula is removed from the vitreous cavity. The spacer 96 is then placed between the positioning system base 80 and the contact extension 82, as shown in FIG. 9.

A localized retinal detachment (the "bleb") is created by using a sub-retinal infusion needle in the macular region, the bleb including the area of choroidal neovascularization. A new retinotomy is created on the temporal edge of the bleb, with the new incision created less than 4 mm away from the fovea to reduce the risk of a peripheral retinal tear. The retinotomy is approximately 1.0-1.3 mm in diameter in order to accommodate the probe. The delivery device probe 18 is then reinserted into the vitreous cavity and into the sub-retinal space through the second retinotomy, as seen in FIG. 10. The distal end of the probe is positioned directly above the target (such as the center of the CNV complex or fovea) with the positioning system touching the sclera, thus insuring the distance of the probe tip is about 1.5 mm above the target area.

Next, the radiation dose is delivered to the target tissue. To this end, the radiation source is advanced by pushing the slider mechanism towards the tip of the probe. Once advanced, the source wire is locked into position by locating the pin in the detent 62. After the appropriate treatment time, the slider mechanism is retracted to bring the radioactive source back to the storage and locked position. After insuring that the radioactive source has been fully retracted into its storage position, the delivery probe is removed from the bleb and withdrawn from the eye.

After removal of the probe, the retina is then reattached intraoperatively, and a complete fluid-air exchange is performed, resulting in an air or gas tamponade in the vitreous cavity. The retinotomy is closed by, e.g., laser photocoagulation, if necessary, while the superior sclerotomy is closed with ophthalmic sutured. The inferotemporal sclerotomy is closed, and the conjunctiva is sutured with appropriate ophthalmic sutures. Antibiotics and steroids may then be administered in the sub-conjuctival space.

In an alternate method, the retina and other non-target tissue during treatment may be shielded and protected by introducing a radiation-attenuating fluid into the bleb that is created by lifting the retina away from the CNV. The fluid can consist of saline, or a fluid with higher attenuation coefficient, such as contrast media. The use of a radiation-attenuating fluid to protect non-target tissue may also be advantageous during epi-retinal and epi-scleral applications of radiation. In such cases, the radiation-attenuating fluid is merely introduced into the vitreous cavity, rather than into the sub-retinal space.

Maintaining the bleb shape during the course of the procedure is also important to minimizing the potential for damage to the photoreceptors. It is contemplated that the bleb shape may be maintained in several different ways. For example, the bleb shape may be maintained by injecting a high viscosity material into the sub-retinal space created by the bleb. Because of the material's high viscosity, its ability to flow through the retinotomy is reduced. The high viscosity material is removed, after treatment, using a standard vitrectomy device. One suitable high density material is a sodium hyaluronate preparation for ophthalmic use sold by Pharmacia Company, under the trademark HEALON®. A substance with variable viscosity having a high initial viscosity during the treatment time, with a lower viscosity thereafter, would further facilitate the removal of the material form the sub-retinal space upon completion of the procedure. A gelatinous substance whose viscosity can be reduced through the administration of a diluting agent (e.g., water), a chemical agent (for adjusting ph), a temperature-charging agent or energy, photo reaction due to light administration, etc., would be suitable.

Figure 15:
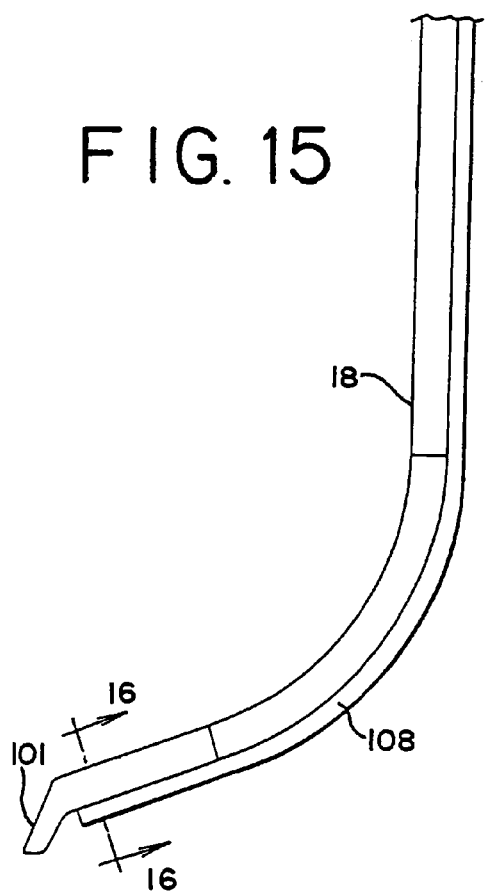
FIG. 15 is a schematic view of a further embodiment of the cannula for use with the present invention in which the cannula includes a lumen for injecting and withdrawing various fluids at the location of the distal end of the cannula.
Figure 16:
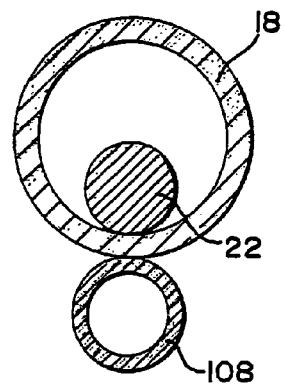
FIG. 16 is a cross-sectional view of the cannula of FIG. 15.

Other methods for maintaining the bleb shape include applying a sealing substance (such as HEALON®) to the retinotomy and the probe/cannula inserted therethrough to prevent the bleb from deflating by blocking the escape of fluid between the probe and the retinotomy. An inflation agent, such as saline, can also be continuously introduced into the sub-retinal space with a small positive pressure by means of an open lumen 108 associated with the cannula 18 (FIGS. 15, 16). Further, the distal end of the cannula can be provided with a balloon (FIG. 12) that is inflated after the distal end of the cannula is introduced into the bleb in order to support the bleb and prevent the bleb from deflating or collapsing.

Figure 17:
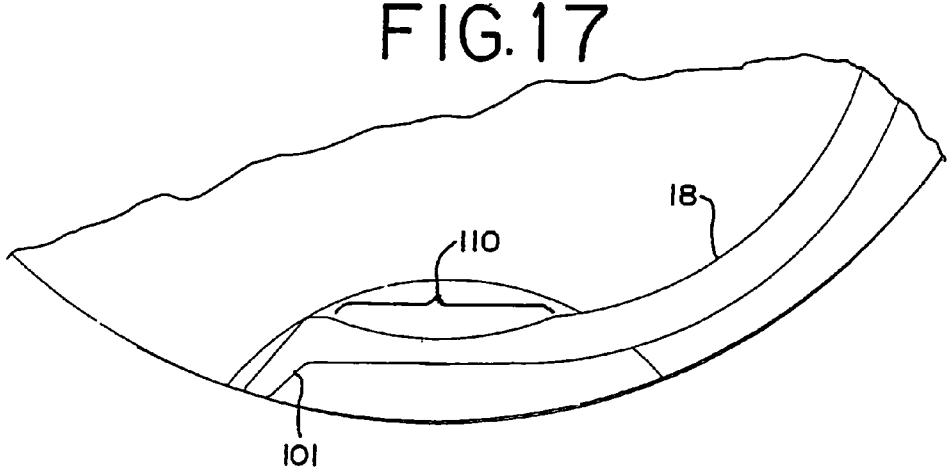
FIG. 17 is a schematic view of a further embodiment of the cannula for use in connection with the present invention in which the non-treatment side of the distal end of the catheter is relieved to minimize contact with the retina.

The need to do a vitrectomy prior to introducing the probe may also be reduced or eliminated if the cannula has a low-friction surface. This can be provided by coating the probe with a lubricant or other coating, such as Teflon or electrolytic carbon, or providing the cannula with a highly-polished surface, as by electro-polishing. Alternatively, the backside 110 of the probe (i.e., the non-treatment side) can be relieved, as shown in FIG. 17, to lessen the degree of contact of the probe with the photoreceptors.

The prevention or limiting of bleeding from the retina into the sub-retinal space, and the removal of any residual blood that should form therein, is also important for protecting the photoreceptors. In this regard, the area of the incision resulting from the vitrectomy performed to create the bleb may be cauterized to prevent or limit retinal bleeding. Such cauterization may be achieved by diathermy, cryopexy, or the application of laser or RF energy using instrumentation and methods known for re-attaching the retina to the retinal pigment epithelium (RPE) in the case of retinal detachment.

Additionally, or alternatively, blood coagulants, such as antihemophilic Factor VIII (recombinant) (available from Bayer Healthcare as Kogenate), aminocaproic acid (available form Immunex as Amicar), and desmopressin acetate (available from Rhone Poulanc Rorer as Octostim), may also be injected into the sub-retinal space to limit bleeding by means of the separate lumen associated with the treatment device, as shown in FIGS. 15, 16. The coagulant may also be removed through the same lumen. Injection of an iron-binding substance (such as apotransferrin) into the blood may also be used in facilitating the removal of blood from the sub-retinal space and preventing its oxidation.

After the CNV has been irradiated, an anti-proliferating drug (anti-Vascular Endothelial Growth Factor or anti-VEGF agent, such as Macugen (pegaptanib sodium), Avastin or Lucentis) may be injected into the sub-retinal space, or applied epiretinally, to prevent and/or limit further growth of the CNV.

It has been observed that hypoxic cells seem to recover better from radiation than healthy cells. Thus, it is believed that it would be beneficial to reduce the retinal blood supply of the non-target tissue during radiation treatment in order to facilitate the recovery of such tissue after being subjected to radiation. To this end, it is proposed that the tip of the probe include an inflatable balloon that causes pressure on the retina when inflated to reduce the blood flow thereto, the radiation treatment being performed through, the balloon. Alternatively, it is proposed to protect the non-target tissue with a deployable mask made of a radiation-blocking material that will be deployed and located over the non-target tissue, while leaving the target tissue exposed. Such a material could be carried by the tip of probe 18 or by a separate device and deployed after formation of the bleb. The material could be biodegradable if desired.

The sub-retinal approach as described above, while believed to be effective in treating AMD, requires an extremely high degree of skill on the part of the ophthalmic surgeon to create the bleb and locate the treatment cannula in the subretinal region. This approach was deemed preferred at one point in time because, despite the surgical challenges, it avoided direct exposure of the retina to radiation. Such protection of the retina was deemed helpful and perhaps even necessary to therapeutic value. Earlier patents even described techniques for irradiating from behind the eye to avoid direct radiation exposure to the retina. See, e.g., U.S. Pat. Nos. 5,637,073 and 6,443,881. However, it has subsequently been determined that in accordance with various aspects of the present invention, AMD may be treated by exposing the sub-retinal target area to ionizing radiation that passes through the retina, without causing undue harm to the retina. In this connection, the delivery device of the present invention may also be used in methods for intraocular, epiretinal application of radiation, in which no bleb is created, and the target tissue is irradiated through the retina.

In the epiretinal application of radiation to the target tissue, only a selected area of the retina—and not the entire retina—is exposed to radiation. The target area or region may be centered on or include the fovea, or the target region may be a separate lesion area, such as an area of leaking blood vessels identified by dye or other visualizations techniques. The target region is typically no more than about 5-6 mm in diameter or width in the illustrated embodiment, and the delivered radiation dosage drops from a peak dosage in the center of the target region to preferably not more than about 20% of the peak dosage at about 3 mm from the center. Outwardly from 3 mm, the delivered radiation dose drops exponentially so that relatively little, if any radiation dosage is delivered substantially outside the target region.

Figure 26:
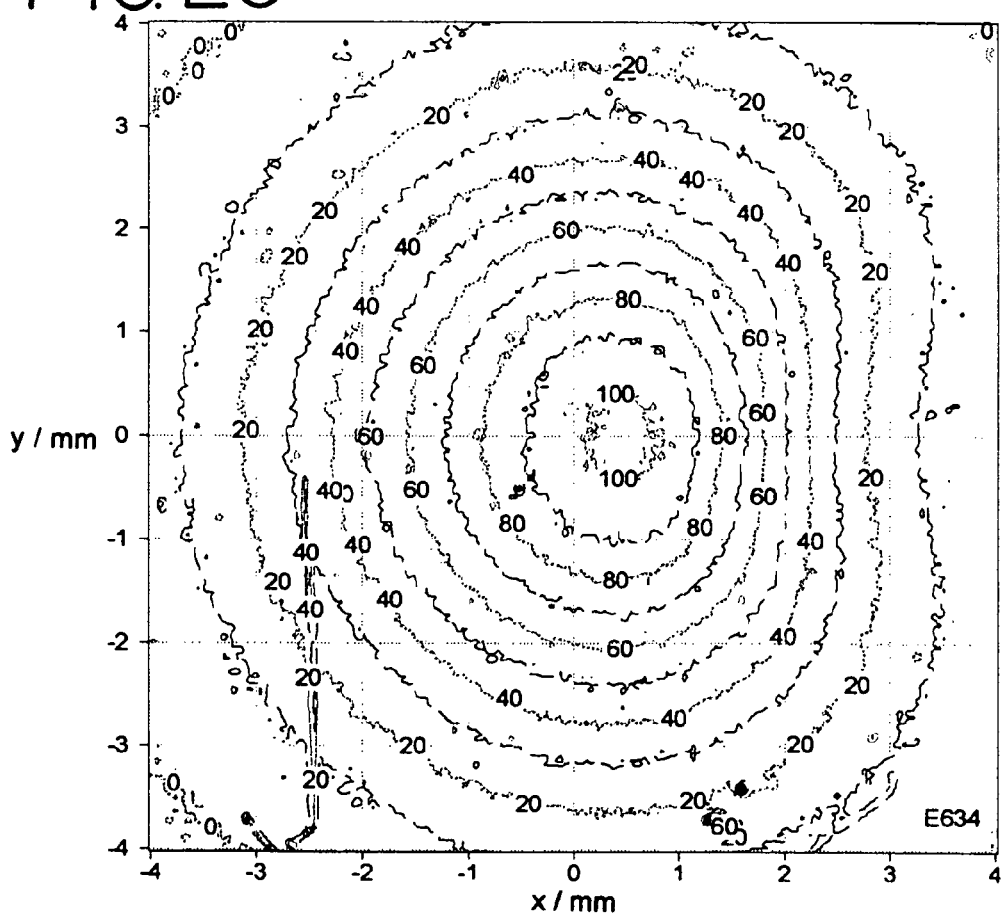

FIG. 26 illustrates a dose distribution as it varies from the center peak value. The X and Y axis generally represent distance from the center and curves or circles within the figure represent the percentage of peak dose. For example, along the X axis it may be seen that the delivered dose at a distance of about 3 mm from the center is about 20% of the peak delivered dose. As can be seen, the dose distribution is not perfectly circular and reference to diameter or distance from center or width is approximate. As the distance increases from the center, the delivered dose drops off rapidly, assuring that area of the retina substantially outside the target area receives minimal radiation exposure. This highly localized application of radiation, which will be discussed in more detail later, minimizes potentially detrimental levels of exposure of the retina to radiation, and is particularly beneficial to maintaining visual acuity.

Figure 18:
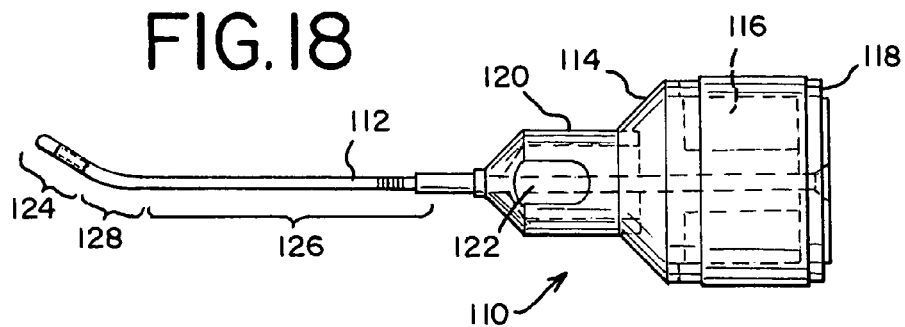
FIG. 18 is a plan view of an alternate embodiment of the cannula and distal end portion of the handpiece for use in the delivery device of FIG. 1.

Thus, in keeping with this aspect of the invention, a radiation delivery device having a distal end particularly suited for the epiretinal application of radiation is disclosed in FIG. 18. The proximal portion of the delivery device and the radiation source wire are similar to one or more of the embodiments described above. The distal end of the delivery device, generally designated 110, includes a cannula 112 that is mounted to the case 42 of the handle 16 of the delivery device. This is accomplished in the illustrated embodiment by means of a central hub 114, outer shield 116, and retaining member 118 that are similar to the central hub 46, outer shield 48, and retaining member 50 described above in connection with FIGS. 1-3. In addition, a grip portion 120 is secured to the distal end of the central hub 114. As illustrated, the grip portion 120 has a generally cylindrical proximal portion and a conical distal portion. The cylindrical portion has opposed flat sections 122 (one such surface shown in FIG. 18). These irregular surfaces 122 facilitate holding the delivery device with a pencil-like grip between the thumb and/or fingers of the surgeon. However, other gripping surfaces may be used as ergonomically appropriate. The flats 122 lie in planes parallel to a plane defined by the cannula and aligned with a positioning sleeve located at the distal end of the cannula to assist in the proper orientation of the cannula and directional application of radiation during a procedure. In addition, the grip portion 120 provides additional shielding of the user from radiation as the radiation source wire is advanced and retracted, as well as provides strain relief at the attachment point of the cannula 112 to the delivery device. The same structure may also be used in the subretinal approach, and the apparatus of FIGS. 1-3 may be modified to include such a gripping/shielding portion.

The cannula 112 is preferably sized to fit through a standard vitrectomy trocar and, thus, has an outside diameter of no more than 1.0 mm. With reference to the specific embodiment illustrated in FIG. 18, the distal end or tip portion 124 of the cannula 112 is formed so that its axis is preferably at an angle α of about 30°, and more preferably of 31.33°, with respect to the axis of the proximal portion 126 of the cannula. A curved transition portion 128 joins the distal end portion to the proximal portion. Alternatively, the cannula 112 may be straight from its proximal end to its distal end, with no bend at the tip.

Figure 19:
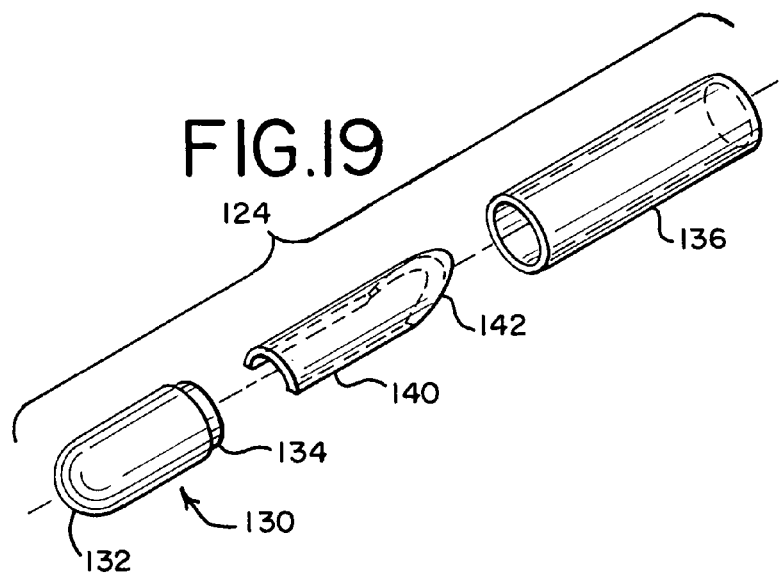
FIG. 19 is an enlarged exploded view of the distal end of the cannula shown in FIG. 18 showing the tip, guide tube and cover sleeve.

The tip portion 124 of the cannula is shown in an exploded view in FIG. 19. It includes a solid tip member 130 having a rounded, non-traumatic end 132 and a shoulder 134 for seating the end of a cover sleeve 136. Other configurations may be employed for the tip member 130, such as the angled configuration shown in FIGS. 12, 15, and 17. The tip 130 may be made of stainless steel, or made from or coated with a softer, atraumatic material such as silicone.

Figure 20:
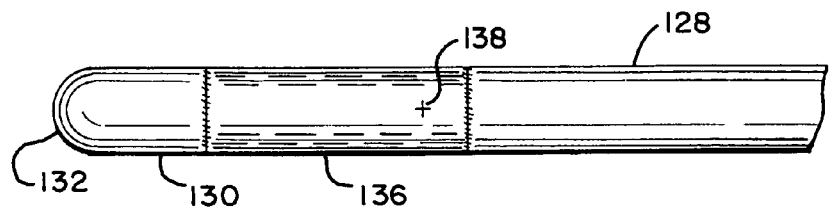
FIG. 20 is an enlarged top view of the distal end of the cannula shown in FIG. 18.
Figure 21:
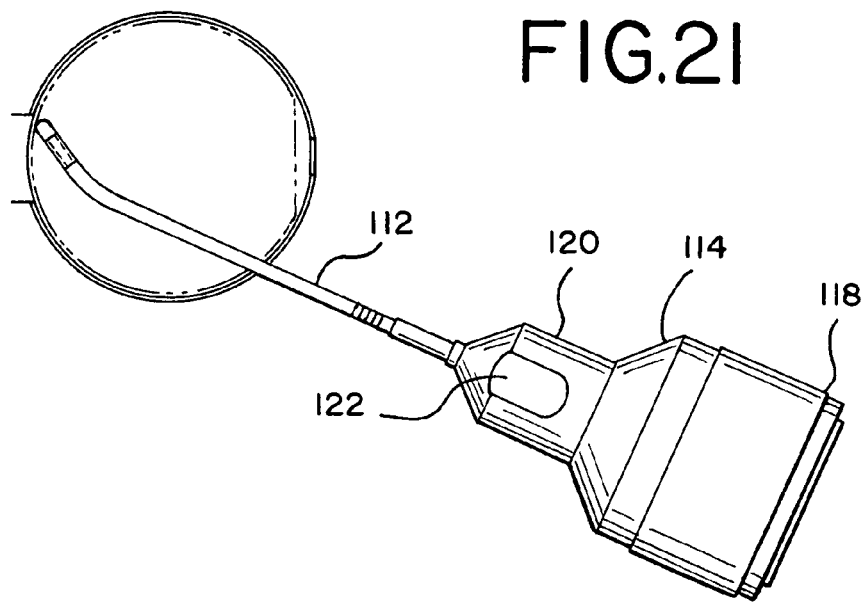
FIG. 21 schematically illustrates the spatial relationship between the tip of the cannula and the target tissue when the device of FIG. 18 is used for the intraocular epiretinal treatment of target tissue.
Figure 22:
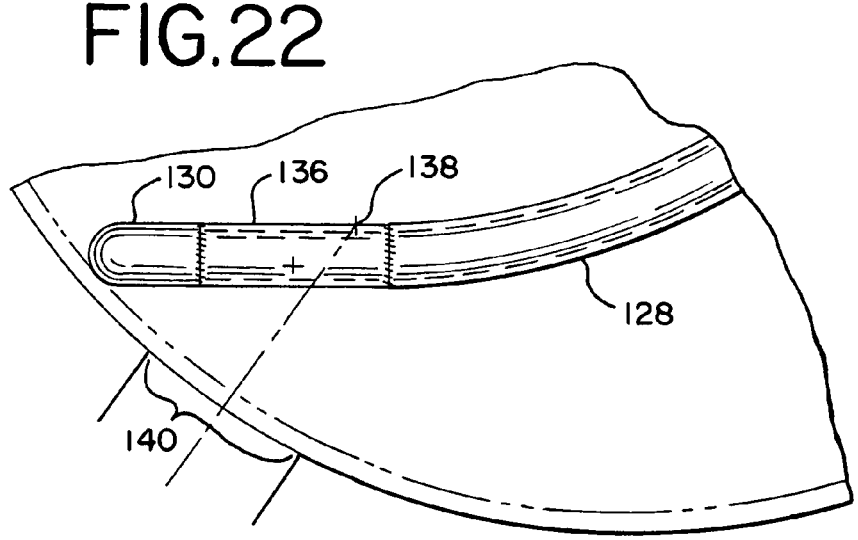
FIG. 22 is a portion of FIG. 21 enlarged to show detail.

With reference to FIG. 20, the distal end of the cannula preferably carries a visual indicator viewable through the lens of the eye during surgery to identify when the radiation source (when introduced into the cannula) will be properly positioned relative to the target area for the desired radiation exposure. In the illustrated embodiment, the top of the cover sleeve 136 is preferably inscribed with a cross-mark 138 located 4.215 mm from the end of the cannula. The cross-mark 138 represents the center of dose distribution and facilitates properly locating the distal end of the cannula 112 with respect to the target tissue by usually centering the cross-mark 138 over the fovea 140 or other target area, as illustrated in FIGS. 21 and 22. As can be appreciated, the position of the cross-mark 138 will vary depending upon the angle α of the tip portion 124 with respect to the axis of the cannula 112. Other indicia or techniques for positioning the distal end of the cannula may also be used as discussed herein. As illustrated, the cover sleeve 136 and tip member 130 have a combined length of 4.75 mm, and comprise the distal-most straight portion of the cannula.

A guide sleeve or partial guide tube 140 may be located interior of the cover sleeve 136, and secured to the tip member 130 by, e.g., laser welding. As the inside diameter of the cannula is slightly larger than the outside diameter of the radioactive source wire to allow for free travel of the source wire between the treatment and retracted positions, the guide tube 140 serves to bias the radiation source into close proximity with the sidewall of the cover sleeve 136 adjacent the target tissue to insure consistent positioning of the radioactive source within the cannula and a more predictable dosing of the target tissue. As mentioned earlier, this position of the radiation source is fixed relative to the gripping flats 122, so that the surgeon knows tactilely that the radiation source is properly oriented relative to the target tissue. The guide tube 140 is only partially radially coextensive with the cover sleeve 136 and, as illustrated, has an arcuate or semicircular cross-section. The proximal end 142 of the guide tube 140 is inclined or beveled to facilitate entry of the tip of the source wire into the distal tip of the cannula. As shown, the bevel is preferably at an angle of 25° with respect to the longitudinal axis of the guide tube 140. The guide tube 140 also provides directional shielding for the non-target tissue.

Performance of the epiretinal method is substantially easier then the subretinal approach. Intraocular access made simply through a sclerotomy, and the distal end of the probe is located over the macula. No detachment of the retina or the creation of a bleb is required. Accurate placement of the probe may be accomplished by any of the positioning systems described. Ultrasound or Doppler techniques known in the art may also be used. Other mechanical methods may also be used, such as putting a stand-off fiber or "whisker" on the tip of the probe that touches the retina when the probe is properly positioned. Alternatively, an inflatable balloon that, when inflated, spaces the probe the desired distance from the target tissue can also be used.

In performing the epiretinal method, the same subject preparation, pre-treatment planning, and accessing of the treatment area are performed as described above in connection with the subretinal approach. Trocars may be placed in the sclerotomy incisions to facilitate the introduction of the various cannulas into the vitreous cavity. The specific geometry/configuration of the cannula and tip may vary. However, the sclerotomy for the entry of the cannula into the eye should always be made the same distance form the surgical limbus—between approximately 3.0-4 mm—, and the tip of the cannula should touch the retina outside of the fovea but within the field of view of the surgical microscope, so that the device can deliver the intended dose to the target tissue.

Next, the treatment probe is positioned. Under microscopic visualization, the cannula 112 is inserted into the vitreous cavity and positioned over the target tissue, using the crossmark 138 on the cannula tip as an alignment aid. The nontraumatic tip is brought into gentle contact with the retina which, because of the geometry of the cannula, will provide the appropriate distance between the center of the radiation source (when the radiation source advanced to the treatment portion of the cannula) and the treatment site of between approximately 2-6 mm, (more preferably approximately 2-3 mm and specifically about 2.6 mm). When the cannula is properly located, the radiation source will deliver the prescribed dose in from approximately 2 to 5 minutes.

To this end, the appropriate gentle contact of the tip of the cannula with the retina may be achieved visually by the surgeon in the following manner. With the cannula inserted into the vitreous cavity so that the tip is located between the retina/target tissue and an endoilluminator, a shadow is cast on the back of the eye that is spaced from the tip of the cannula. As the cannula is moved toward retina/target tissue, the shadow converges toward the cannula and the lighted area between the shadow and the cannula becomes smaller. The lighted area is eliminated as the tip of the cannula touches the retina/target tissue, thus indicating to the surgeon contact of the cannula with the retina.

Next, the radiation dose is delivered to the target tissue by advancing the radiation source with the slider mechanism, as described above. After the appropriate treatment time, the slider mechanism is retracted to bring the radioactive source back to the storage and locked position. The delivery probe is then withdrawn from the eye. After removal of the probe, the sclerotomy is closed using conventional surgical techniques and the infusion needle removed. The conjunctiva is closed and antibiotics and steroids are administered in the sub-conjunctival space.

As can be appreciated, when the cannula is located by gently touching the retina, as described above, the spacing between the radiation source and the target tissue may vary depending upon the shape of the cannula, (i.e., straight shaft or bent shaft) and the geometry of the tip (e.g., angled—FIGS. 12, 15, 17, or straight/blunt—FIGS. 18-22). The greater the space between the radiation source and the target tissue, the longer the exposure time required to deliver a specified dose to the target tissue. However, the greater the space between the radiation source and the target tissue, the flatter the dose profile (i.e., the more even the dosing) for the target tissue.

The radiation source preferably has an activity level of approximately 5-20 mCi, and is more preferably approximately 11-13 mCi. The dose delivered to the target tissue may vary from between about 7 Gy (the lowest dose currently believed to be therapeutically effective) and 50 Gy (the dose for which initial signs of radiation acute toxicity have been observed). It is presently contemplated that the preferred dosage will not exceed about 30 Gy and will be in a range of from 20-30 Gy. Therefore, the preferred dosage directed to the target tissue, which may be centered above the fovea or centered above a lesion site spaced from the fovea, depending on the surgeon's selection, is preferably between about 7 and 50 Gy, with a more preferred range between 20 and 30 Gy. A peak dose of about 24 Gy is presently deemed most preferable.

It is also desirable to deliver the desired radiation dose in from between 2 to 5 minutes. This treatment time serves to minimize surgical complications, while still delivering a prescribed radiation dose from a source within an acceptably-low activity level.

As noted earlier, the area of the retina outside the target region is exposed to significantly less radiation, with the amount of delivered radiation dose decreasing exponentially from the target center. Referring, for example, to FIG. 26, the delivered dose is about 20% of the peak at about 3 mm from the center. Thus, the delivered dose at this distance may vary from about 1.4 Gy to about 10 Gy for a peak dose of 7-50 Gy, and from about 4 Gy to 6 Gy for a preferred peak dose of 20-30 Gy. The dosage drops off quickly so that radiation exposure is substantially limited to the target area, and dosage outside the target area is less than about 10 Gy and more preferably less than 6 Gy in the vicinity of the retina adjoining the target region decreasing significantly with increased distance beyond the target region.

Figure 23:
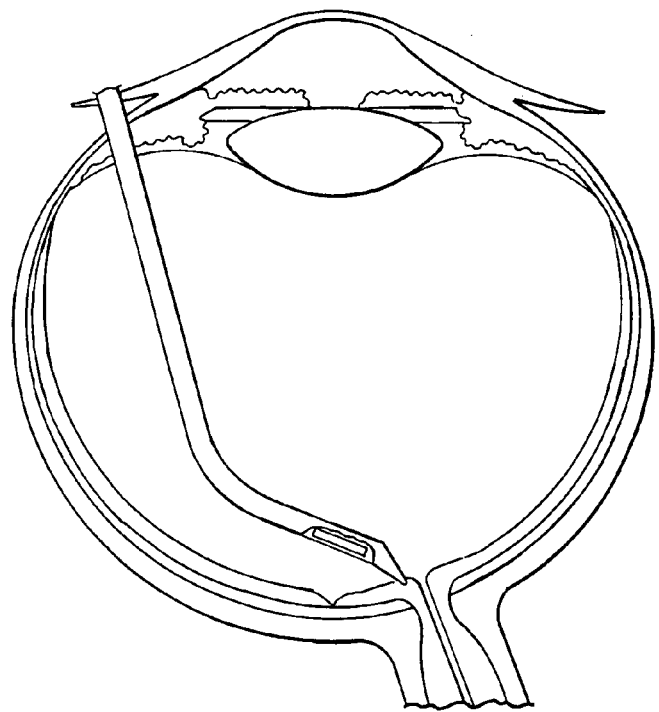
FIGS. 23 and 24 illustrate placement of the treatment cannula in performing the irradiation of the target tissue by the epiretinal method.
Figure 24:
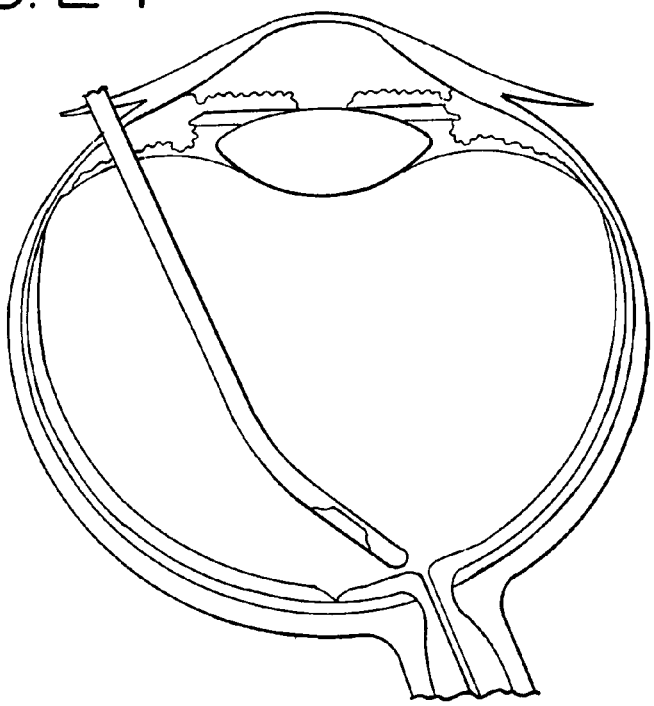
Figure 25:
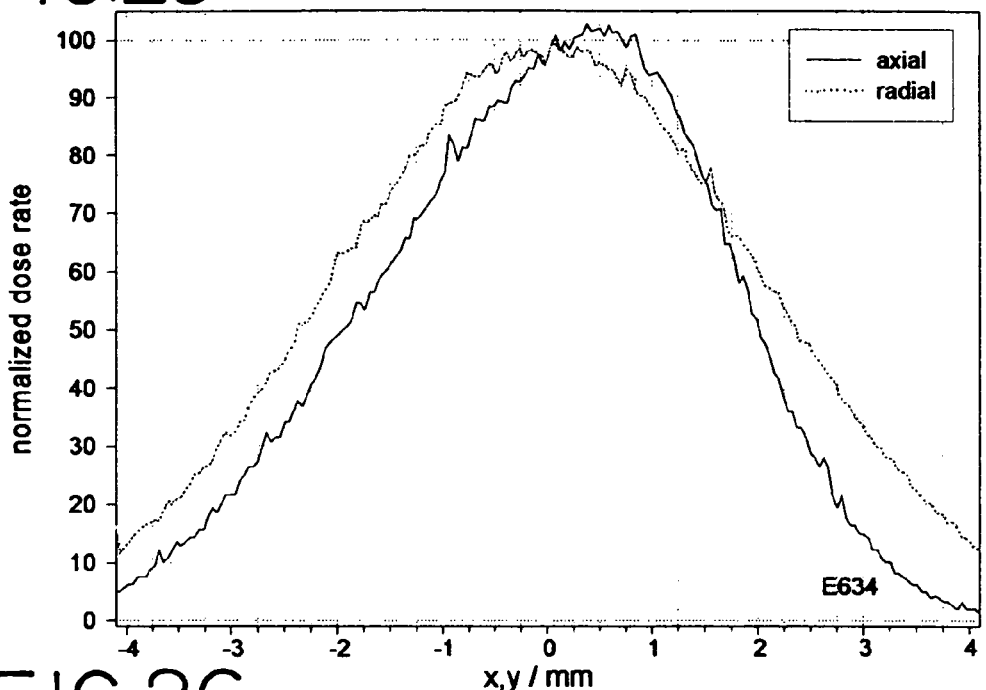
FIGS. 25 and 26 show normalized does profiles for a treatment cannula as illustrated in FIG. 24.

By way of example, with the use of a delivery cannula of the type described above for use in an epi-retinal procedure and having an angled tip 130, as shown in FIGS. 12, 15 and 17, the center of the source is spaced about 2.6 mm from the retina, as generally illustrated in FIG. 23. With a source having an activity level of approximately 6 mCi, a 15 Gy peak dose was delivered in 3-5 minutes. With a tip 130 as shown in FIGS. 18-22, a similar spacing of 2.6 mm from the center of the source to the retina is obtained, as generally illustrated in FIG. 24. With a source activity of 11 mCi, a peak dose of 24 Gy was delivered in 3-5 minutes. FIGS. 25 and 26 are normalized dose rate profiles for the treatment cannula of FIG. 24, showing the does rate distribution axially and radially with respect to the radioactive source (FIG. 25) and topographically (FIG. 26). If the cannula has a straight shaft, the center of the radiation source will be spaced approximately 4 mm from the retina, and it is contemplated that the source will have an activity level of 20 mCi in order to deliver the prescribed dose in the appropriate amount of time.

Although the radiation source is described as a beta radiation emitting source, other ionizing radiation sources may be used, such as gamma or X-ray sources. Such sources may require different exposure times, spacing from the target area and shielding to afford therapeutic benefit without undue harm to non-target areas of the retina. Potential miniature X-ray sources may include sources such as those described in published U.S. applications Nos. 2003/0179854 A1 and 2005/0038488 A1, both of which are incorporated by reference herein. In general, beta radiation and soft X-ray radiation, which may be selected to mimic the characteristics of beta radiation with low energy voltage sources, are presently preferred to reduce or minimize the volume of the radiation to which the body is exposed. However, with precautions and added shielding, gamma or other ionizing radiation may also be suitable.

In a further alternative for locating the radiation source with respect to the target tissue, a miniature radiation sensor that can be remotely interrogated may be placed on the retinal surface, and the distance between the probe tip and the surface of the retina can be determined based upon the level of radiation measured by the sensor. If multiple (i.e. 3) sensors are used, triangulation of the measured radiation intensity would provide an accurate measurement of position. If multiple (i.e. 3) sensors are used, triangulation of the measured radiation intensity would provide an accurate measurement of position. If at least three miniature event counters or sensors are positioned in an array on the periphery of the retina equidistant from the target tissue, the intensity/frequency of events measured by each point can be analyzed and then compared. The position of source then can be determined through well-known three-dimensional triangulation calculations at the beginning of the radiation administration. The event counters/sensors can be placed either in the eye, behind the eye, or even on the front surface of the eye, if the radiation source produced a sufficient emission to be measured externally. Alternatively, the radiation source can carry a small transducer on its tip that would emit a "ping" that can be picked up by receivers positioned as described above. Other signaling/receiving systems such as light or RF can also be used. As a further method, a permanent magnet disposed on the tip of the device could produce a sufficient Galvanic effect in appropriate sensors to be measurable, especially in an epi-retinal application where the size constraints of the device are less critical. A digitally-enclosed signal would provide improved speed and accuracy.

It will be understood that the embodiments and methods of the present invention that have been described are illustrative of the application of the principles of the present invention. Numerous modifications may be made by those skilled in the art without departing from the true spirit and scope of the invention, including combinations of the features that are individually disclosed or claimed herein.

What is claimed:

1. A method for epiretinal treatment of a subretinal target tissue in an eye having a sclera and a retina, comprising the steps of:
    introducing an ionizing radiation source through the sclera into the interior of the eye;
    locating the radiation source with respect to the subretinal target tissue to expose the target tissue to radiation passing through the retina; and
    irradiating the target tissue through the retina with an effective amount of radiation.

2. The method of claim 1 wherein the radiation source delivers a dose of between about 7 and 50 GY.

3. The method of claim 2 wherein the dose is between approximately 20 and 30 GY.

4. The method of claim 3 wherein the dose is approximately 24 GY.

5. The method of claim 1 wherein the radiation source is a beta emitting isotope having a source activity level of between approximately 5-20 mCi.

6. The method of claim 1 wherein the radiation source is a beta emitting isotope having a source activity of between approximately 11-13 mCi.

7. The method of claim 1 wherein the radiation source is spaced from 2-6 mm from the target tissue.

* * * * *